US 10,724,070 B2

(12) United States Patent
Hassett et al.

(10) Patent No.: US 10,724,070 B2
(45) Date of Patent: Jul. 28, 2020

(54) MODIFIED BACTERIAL PATHOGENS AND METHODS FOR EFFECTUATING RAPID RESPONSE TO CONTAMINATION BY KNOWN OR UNKNOWN BACTERIAL PATHOGENS

(71) Applicants: Daniel J. Hassett, Cincinnati, OH (US); Shengchang Su, Cincinnati, OH (US); Thomas J. Lamkin, Cincinnati, OH (US); Roland Saldanha, Cincinnati, OH (US)

(72) Inventors: Daniel J. Hassett, Cincinnati, OH (US); Shengchang Su, Cincinnati, OH (US); Thomas J. Lamkin, Cincinnati, OH (US); Roland Saldanha, Cincinnati, OH (US)

(73) Assignees: University of Cincinnati, Cincinnati, OH (US); Government of the United States as Represented by the Secretary of the Air Force, Wright-Patterson AFB, OH (US)

( * ) Notice: Subject to any disclaimer, the term of this patent is extended or adjusted under 35 U.S.C. 154(b) by 125 days.

(21) Appl. No.: 14/080,247

(22) Filed: Nov. 14, 2013

(65) Prior Publication Data
US 2014/0378343 A1  Dec. 25, 2014

Related U.S. Application Data

(60) Provisional application No. 61/726,126, filed on Nov. 14, 2012.

(51) Int. Cl.
*C12Q 1/18* (2006.01)
*C07K 14/435* (2006.01)
(52) U.S. Cl.
CPC .......... *C12Q 1/18* (2013.01); *C07K 14/43595* (2013.01)
(58) Field of Classification Search
None
See application file for complete search history.

(56) References Cited

U.S. PATENT DOCUMENTS

2007/0112048 A1* 5/2007 Bavari ............... A61K 31/4184
514/367
2008/0248066 A1* 10/2008 Dubensky ............. A61K 39/07
424/248.1
2010/0234287 A1* 9/2010 Inouye ................ C12Q 1/6818
514/2.4

FOREIGN PATENT DOCUMENTS

WO  WO99/07861  *  2/1999

OTHER PUBLICATIONS

Lehtinen et al., J. Microbioligcal Methods, 55:173-186, 2003.*
Janes et al., Inf. Imm.:1949-1993 (Year: 2006).*
Collins et al., Natimicrob. Agents and Chemoth., 42, 2, 344-347 (Year: 1998).*
Zafer et al., Appl. Envi. Microbiol, 67,3,1239-1245 (Year: 2001).*
http://www.niaid.nih. gov/topics/BiodefenseRelated/Biodefense/Documents/category_a_progess_report.pdf, 2003.
http://www.niaid.nih.gov/topics/BiodefenseRelated/Biodefense/Documents/ categorybandc.pdf), 2003.
Su et al. Characterization of stable, constitutively expressed, chromosomal green and red fluorescent transcriptional fusions in the select agent bacterium, *Francisella tularensis* Shu S4 and the surrogate type B live vaccine strain (LVS). Applied Microbiology Biotechnology (2013) 97:9029-9041.
Zaide et al., Identification and Characterization of Novel and Potent Transcription Promoters of *Francisella tularensis*. Applied and Environmental Microbioloy, (2011) 77: 1608-1618.)
Norris, M. H. et al., Glyphosate resistance as a novel select-agent-compliant, non-antibiotic-selectable marker in chromosomal mutagenesis of the essential genes asd and dapB Burkholderia pseudomallei. Applied and Environmental Microbiology (2009), p. 6062-6075, vol. 75, No. 19.
Wehrly, T.D. et al. (2009) Intracellular biology and virulence determinants of *Francisella tularensis* revealed by transcriptional profiling inside macrophages. Cell Microbiol 11(7):1128-50. NCBI GEO database.

* cited by examiner

*Primary Examiner* — Nancy A Treptow
(74) *Attorney, Agent, or Firm* — Dinsmore & Shohl LLP

(57) ABSTRACT

Stable, constitutively expressed, chromosomal fluorescent transcriptional fusions in bacterial pathogens and methods of using the same to screen candidate compounds for antibacterial efficacy.

7 Claims, 22 Drawing Sheets

Figure 1A:
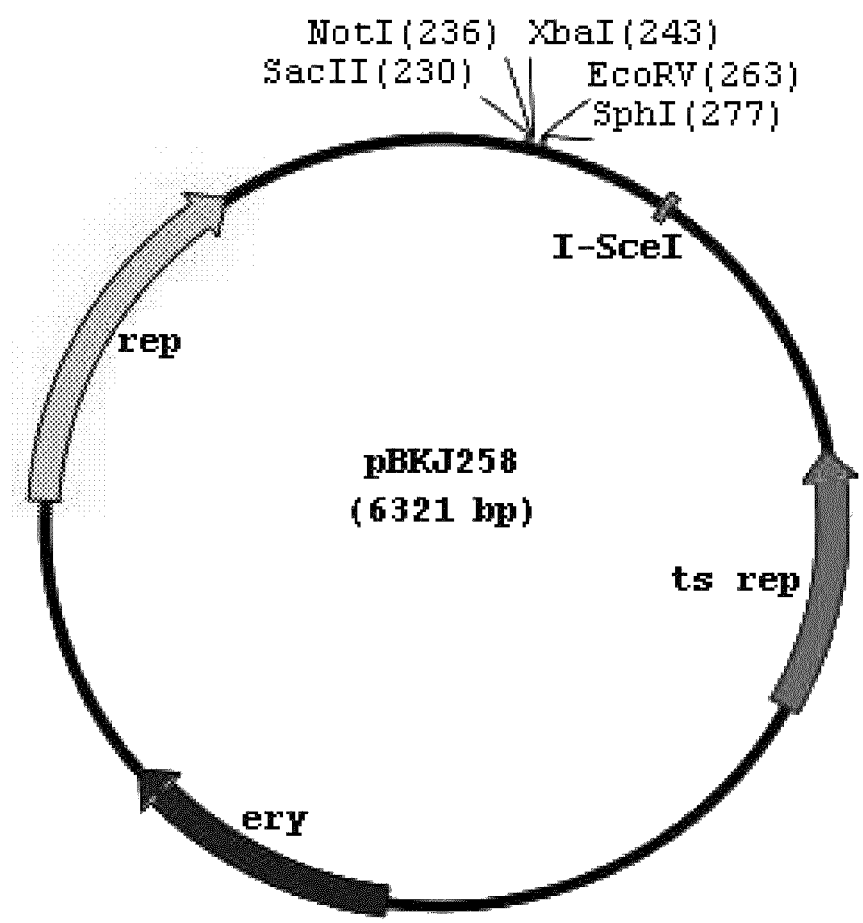

Fig. 3A
Fig. 3B
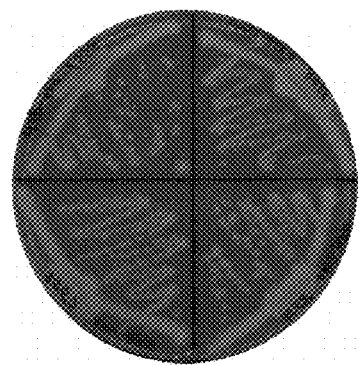
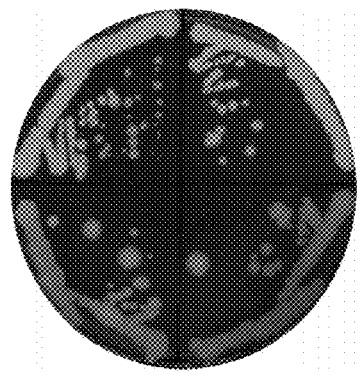
Fig. 3C
Fig. 3D
| DH5α pntr-GFP 1.2s | DH5α p0253-GFP 1.2s | Stern pntr-GFP 1.2s | Stern p0253-GFP 200ms |
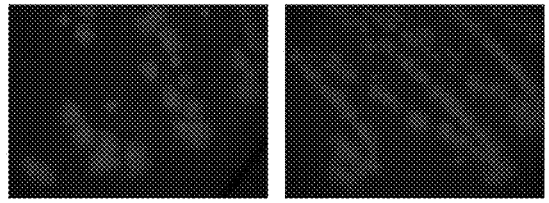
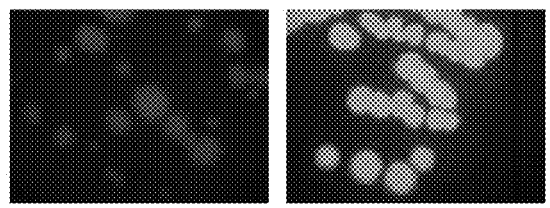
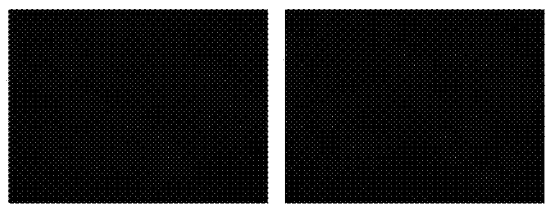
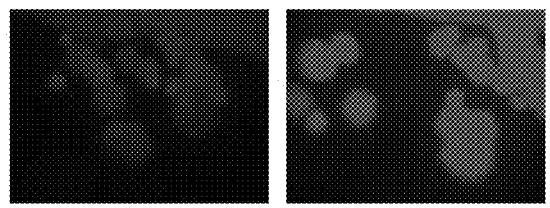
| DH5α pntr-RFP 3s | DH5α p0253-RFP 3s | Stern pntr-RFP 1.2s | Stern p0253-RFP 200ms |

Fig. 4A

B. anthracis GFP vegetative cells

Fig. 4B

B. anthracis GFP spores

Fig. 4C

MDM's infected with B. anthracis superfolder spores

Fig. 7A

Y. pseudotuberculosis GFP

Fig. 7B

CO92 GFP

Fig. 7C

CO92 RFP pMP749-p1794-GFP    pMP749-prpsF-GFP    pMP749-prpsF-RFP pMP749-p1794-GFP    pMP749-prpsF-GFP    pMP749-prpsF-RFP pMP749-prpsF-GFP    pMP749-prpsF-RFP

Fig. 11A
E. coli E2071
(pmini-Tn7-gat-P1-GFP
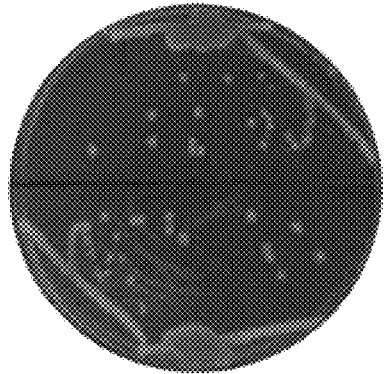
Fig. 11B
B. thailanderensis
Tn7-P1-GFP
Fig. 11C
E. coli E2071
(pmini-Tn7-gat-P1-RFP
Fig. 11D
B. thailanderensis
Tn7-P1-RFP
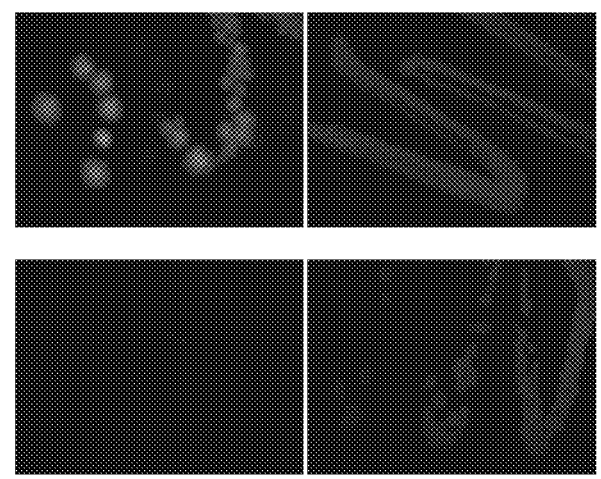

Fig. 12A

GFP-tagged B. thailandensis

Fig. 12B

RFP-tagged B. thailandensis

Fig. 12C

GFP-tagged B. mallei

Fig. 12D

GFP-tagged B. pseudomallei

Fig. 12E

Phagocytized GFP-tagged B. mallei
Phagocytosis for 90 mins. 20X
THP-1 macrophage

MODIFIED BACTERIAL PATHOGENS AND METHODS FOR EFFECTUATING RAPID RESPONSE TO CONTAMINATION BY KNOWN OR UNKNOWN BACTERIAL PATHOGENS

CROSS REFERENCE TO RELATED APPLICATION

This application claims benefit to U.S. Provisional Application Ser. No. 61/726,126, filed Nov. 14, 2012, which is incorporated by reference herein in its entirety.

GOVERNMENT RIGHTS

This invention was made with government support under FA8650-08-C-6832 awarded by AFMCLO/JAZ. The government has certain rights in the invention.

TECHNICAL FIELD

This invention relates to stable and constitutively expressed chromosomal fluorescent transcriptional fusions in bacterial pathogens and methods for rapid identification of anti-bacterial agents in response to contamination by bacterial pathogens, in particular in response to contamination due to bioterrorism or biowarfare.

BACKGROUND

The U.S. Centers for Disease Control and Prevention (CDC) defines a bioterrorism attack as the deliberate release of viruses, bacteria, or other germs (agents) used to cause illness or death in people, animals, or plants. According to the CDC, these agents are typically found in nature, but it is possible that they could be changed to increase their ability to cause disease, make them resistant to current medicines, or to increase their ability to be spread into the environment. The CDC warns that these biological agents can be spread through the air, through water, or in food, and that terrorists may use biological agents because they can be extremely difficult to detect and do not cause illness for several hours to several days.

The 2001 anthrax attacks are the most recent bioterrorism attack in the United States. Since these attacks, the United States and the Animal and Plant Health Inspection Services, the CDC, and the National Institutes of Allergy and Infectious Disease have initiated numerous research-based programs designed to better understand the pathogenic mechanisms of many bacteria and viruses that are capable of causing significant and highly problematic human disease and death. The U.S. Department of Health and Human Services or the U.S. Department of Agriculture has declared bio-agents that potentially pose a severe threat to public health and safety as select agents, and categorizes these select agents as Category A, B or C according their ease of dissemination and mortality and morbidity rates, among other factors.

Given the relative ease of genetic manipulation in bacterial pathogens based on technology developed in recent years, coupled with the dramatic increase in antibiotic resistance in virtually all bacterial pathogens, it is a distinct possibility that skilled scientists motivated to trigger a bioterrorist attack would be likely to engineer bacterial pathogen strains that are resistant to all current antibiotic regimens. Upon release and contamination, genetically engineered bacterial strains must be characterized and scientists will urgently have to screen novel chemical libraries for compounds that could kill these new antibiotic resistant strains without being toxic themselves to human cells, and in a time frame that prevents catastrophic population decimation.

There are many well-characterized libraries of chemical compounds with proven safety profiles already in the United States that could be screened for antibiotic efficacy against potentially new antibiotic-resistant strains of bacterial pathogens. However, in order to achieve the time-effective high throughput screening that would be necessary to provide a rapid response to intentional contamination, a platform providing a simple read-out for death and/or growth inhibition of these highly virulent bacterial pathogens is most desirable.

Simple read-out technologies are known in the art. For example, one such simple read-out based on death and/or growth inhibition is accomplished through the use bacterial pathogens and surrogates that have been genetically engineered to incorporate fluorescent protein reporters. As long as these genetically engineered bacterial pathogens are alive, the organism fluoresces, yielding a visible signal. Upon the death of the genetically engineered pathogen, the organism no longer fluoresces. Although such technology is known, it has not previously been considered in the development of counter-bioterrorism technology.

However, for the fluorescent protein reporters to be useful for high-throughput screening of large libraries of candidate compounds in the context of mounting a counter-bioterrorism response, the fluorescent measurements must require extremely short exposure time, as the cumulative exposure time of large libraries should be kept to a minimum. Ideally, less than 200 ms exposure time should be required to provide a salient read-out signal. The present inventors are unaware of existing fluorescent protein reporters at the single copy level in bacterial pathogen select agents that can meet such a short exposure requirement.

As such, there is a need for bacterial pathogens comprising fluorescent transcriptional fusion reporters capable of measurable signaling in a time frame suitable for rapid identification of an anti-bacterial agent. More effective methods for providing a rapid response to a bacterial contamination resulting from, for example, bioterrorism are also needed. In particular, there is a need for methods of screening candidate compounds for anti-bacterial efficacy useful for countering intentional contamination by altered bacterial pathogens resistant to existing antibacterial agents.

SUMMARY

Accordingly, the present inventors have developed strains of modified bacterial pathogens comprising stable and constitutively expressed chromosomal green and red fluorescent transcriptional fusions capable of providing simple read-out data in unexpectedly short exposure times, making them particularly suitable for rapid screening of candidate compounds for anti-bacterial efficacy. Methods utilizing these reagents for launching time-effective rapid response to massive contamination by, for example, antibiotic-resistant strains of bacterial pathogens are also provided. Specific embodiments are direct to stable and constitutively expressed chromosomal green and red fluorescent transcriptional fusions in Category A, B or C bacterial pathogens and methods of using the same to screen candidate compounds in high-throughput screening for anti-bacterial efficacy are disclosed herein.

One embodiment of the presently-disclosed subject matter is directed to a method of screening candidate compounds for possessing anti-bacterial efficacy suitable for rapid response to contamination by a bacterial pathogen. The method comprises the steps of: providing a modified bacterial pathogen, wherein the modification comprises a plasmid insert, said plasmid insert engineered to constitutively express a chromosomal transcriptional fusion fluorescent protein that results in sustained fluorescence while the modified bacterial pathogen is alive; contacting a candidate compound with the modified bacterial pathogen; determining whether the modified bacterial pathogen exhibits fluorescence; and identifying a candidate compound as comprising anti-bacterial efficacy where the fluorescence is extinguished.

Another embodiment is directed to a *Bacillus anthracis* cell genetically engineered with a plasmid insert to constitutively express a chromosomal transcriptional fusion fluorescent protein, wherein said plasmid insert is selected from the group consisting of pBJKΔBla1-p0253-GFP, pBJKΔBla1-p0253-RFP, pBKJΔBla1-pntr-GFP, pBKJΔBla1-pntr-RFP, pRP1028ΔBla1-p0253-GFP, and pRP1028ΔBla1-p0253-RFP.

An additional embodiment is directed to a *Yersina pestis* cell genetically engineered with a plasmid insert to constitutively express a chromosomal transcriptional fusion fluorescent protein, wherein said plasmid insert is selected from the group consisting of pUC18-R6KT-mini-Tn7T-Km-2pcysZK-GFP and pUC18-R6KT-mini-Tn7T-Km-2pcysZK-RFP.

A further embodiment is directed to a *Francisella tularesis* cell genetically engineered with a plasmid insert to constitutively express a chromosomal transcriptional fusion fluorescent protein, wherein the plasmid insert is selected from the group consisting of pMP749-prpsF-GFP, pMP749-prpsF-RFP, pMP749-p1794-GFP, and pMP749-p1749-RFP.

Another embodiment is directed to a *Burkholderia* cell genetically engineered with a plasmid insert to constitutively express a chromosomal transcriptional fusion fluorescent protein, wherein the plasmid insert is selected from the group consisting of pmini-Tn7-gat-P1-GFP and pmini-Tn7-gat-P1-RFP.

According to another embodiment, a method of responding to intentional bioterroristic dissemination of a known or unknown bacterial pathogen is provided. The method comprises isolating a sample cell of the known or unknown bacterial agent; modifying the cell by inserting a plasmid engineered to constitutively express a chromosomal transcriptional fusion fluorescent protein that results in sustained fluorescence while the modified bacterial pathogen is alive; screening a library of anti-bacterial agents for efficacy against the known or unknown bacterial pathogen, said screening comprising the steps of: contacting a candidate compound with the modified bacterial pathogen; determining whether the modified bacterial pathogen exhibits fluorescence; and identifying a candidate compound as comprising anti-bacterial efficacy against the known or unknown bacterial agent where the fluorescence is extinguished; treating the contamination with the identified antibacterial compound.

These and additional aspects and features of the instant invention will be clarified by reference to the figures and detailed description set forth herein.

BRIEF DESCRIPTION OF THE DRAWINGS

FIG. 1A shows a schematic representation of the plasmid pBJK258 vector. FIG. 1B shows a schematic representation of the plasmid pBJKΔBla1-p0253-GFP vector. FIG. 1C shows a schematic representation of the plasmid pBJKΔBLA1-p0253-RFP vector.

FIG. 2A shows a schematic representation of the plasmid pRP1028 vector. FIG. 2B shows a schematic representation of the plasmid pRP1028-p0253-GFP vector. FIG. 2C shows a schematic representation of the plasmid pRP1028-p0253-GFP vector.

FIG. 3A shows *E. coli* DH5-α strains harboring with vector plasmids pBKJΔBla1-pntr-GFP (top left quadrant), pBKJΔBla1-pntr-RFP (bottom left quadrant), pBKJΔBla1-p0253-GFP (top right quadrant), and pBKJΔBla1-p0253-RFP (bottom right quadrant) struck on L-agar plates. FIG. 3B shows *Bacillus anthracis* Stern chromosomally integrated with vector plasmids pBKJΔBla1-pntr-GFP (top left quadrant), pBKJΔBla1-pntr-RFP (bottom left quadrant), pBKJΔBla1-p0253-GFP (top right quadrant), and pBKJΔBla1-p0253-RFP (bottom right quadrant) struck out on L-agar plates. FIG. 3C shows colony fluorescence micrographs of *E. coli* DH5-α strains harboring with vector plasmids pBKJΔBla1-pntr-GFP (top left quadrant), pBKJΔBla1-pntr-RFP (bottom left quadrant), pBKJΔBla1-p0253-GFP (top right quadrant), and pBKJΔBla1-p0253-RFP (bottom right quadrant). FIG. 3D shows colony fluorescence micrographs of *Bacillus anthracis* Stern chromosomally integrated with vector plasmids pBKJΔBla1-pntr-GFP (top left quadrant), pBKJΔBla1-pntr-RFP (bottom left quadrant), pBKJΔBla1-p0253-GFP (top right quadrant), and pBKJΔBla1-p0253-RFP (bottom right quadrant).

FIG. 4A shows fluorescence microscopy of *Bacillus anthracis* vegetative cells. FIG. 4B shows fluorescence microscopy of *Bacillus anthracis* spores chromosomally integrated with pRP1028ΔBla1-p0253-GFP. FIG. 4C shows fluorescence microscopy of *Bacillus anthracis* spore chromosomally integrated with pRP1028ΔBla1-p0253-GFP within monocyte derived macrophages.

FIG. 5A shows a schematic representation of the plasmid pUC18R6KT-mini-Tn7T-Km vector. FIG. 5B shows a schematic representation of the plasmid pUC18-R6KT-mini-Tn7T-Km-2pcysZK-GFP vector. FIG. 5C shows a schematic representation of the plasmid pUC18-R6KT-mini-Tn7T-Km-2pcysZK-RFP vector.

FIG. 6A shows *E. coli* DH5-αλ pir strains harboring with vector plasmids pUC18-R6KT-mini-Tn7T-Km-2pcysZK-GFP (top right and left quadrants) and pUC18-R6KT-mini-Tn7T-Km-2pcysZK-RFP (bottom right and left quadrants) struck on L-agar plates. FIG. 6B. shows *Yersinia pseudotuberculosis* chromosomally integrated with vector plasmids pUC18-R6KT-mini-Tn7T-Km-2pcysZK-GFP (top right and left quadrants) and pUC18-R6KT-mini-Tn7T-Km-2pcysZK-RFP (bottom right and left quadrants) struck on L-agar plates. FIG. 6C shows colony fluorescence micrographs of *E. coli* DH5-αλ pir strains harboring with vector plasmids pUC18-R6KT-mini-Tn7T-Km-2pcysZK-GFP (top right and left quadrants) and pUC18-R6KT-mini-Tn7T-Km-2pcysZK-RFP (bottom right and left quadrants). FIG. 6D colony fluorescence micrographs of *Yersinia pseudotuberculosis* chromosomally integrated with vector plasmids pUC18-R6KT-mini-Tn7T-Km-2pcysZK-GFP (top right and left quadrants) and pUC18-R6KT-mini-Tn7T-Km-2pcysZK-RFP (bottom right and left quadrants)

FIG. 7A shows fluorescence microscopy of *Y. pseudotuberculosis* chromosomally integrated with vector plasmid pUC18-R6KT-mini-Tn7T-Km-2pcysZK-GFP. FIG. 7B shows fluorescence microscopy of *Yersinia pestis* CO92 chromosomally integrated with vector plasmid pUC18-

R6KT-mini-Tn7T-Km-2pcysZK-GFP. FIG. 7C shows fluorescence microscopy of *Yersinia pestis* CO92 chromosomally integrated with vector plasmid pUC18-R6KT-mini-Tn7T-Km-2pcysZK-RFP.

Figure 8A:
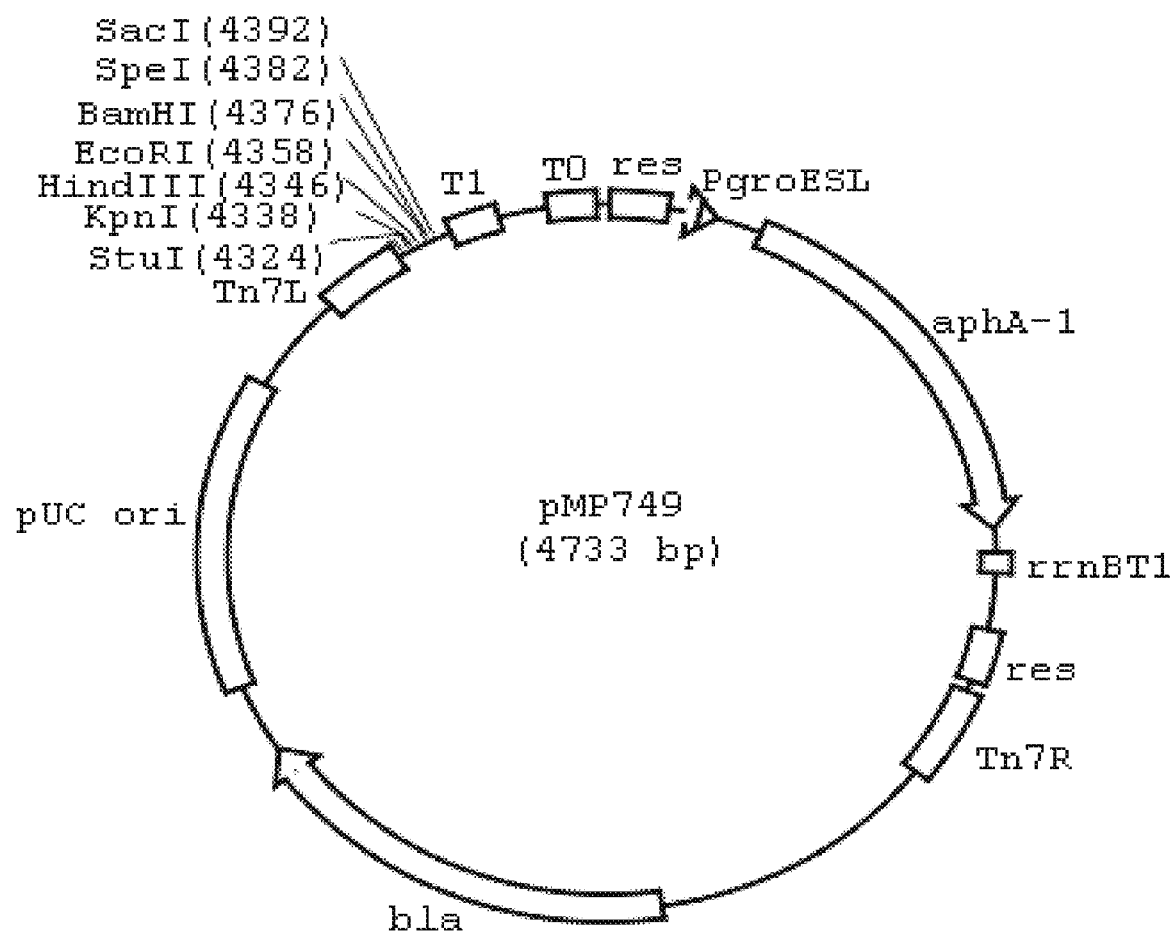
Figure 8B:
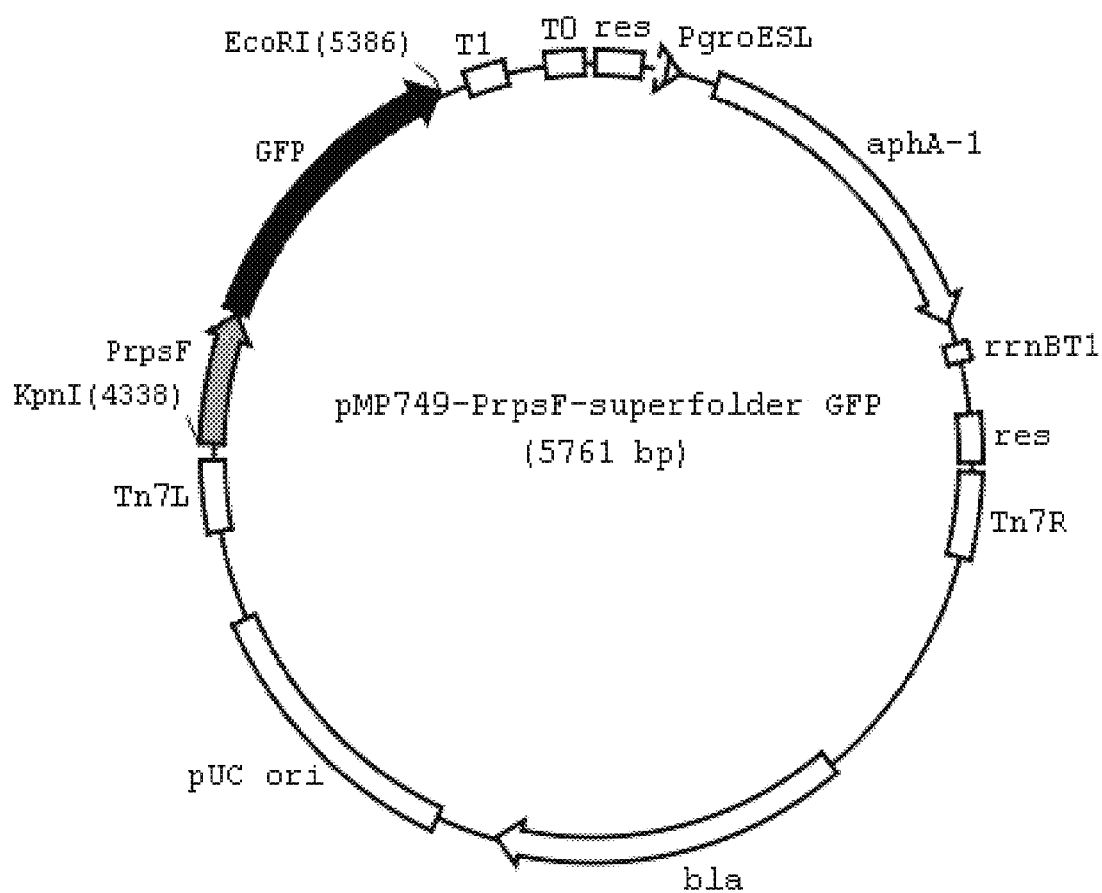
Figure 8C:
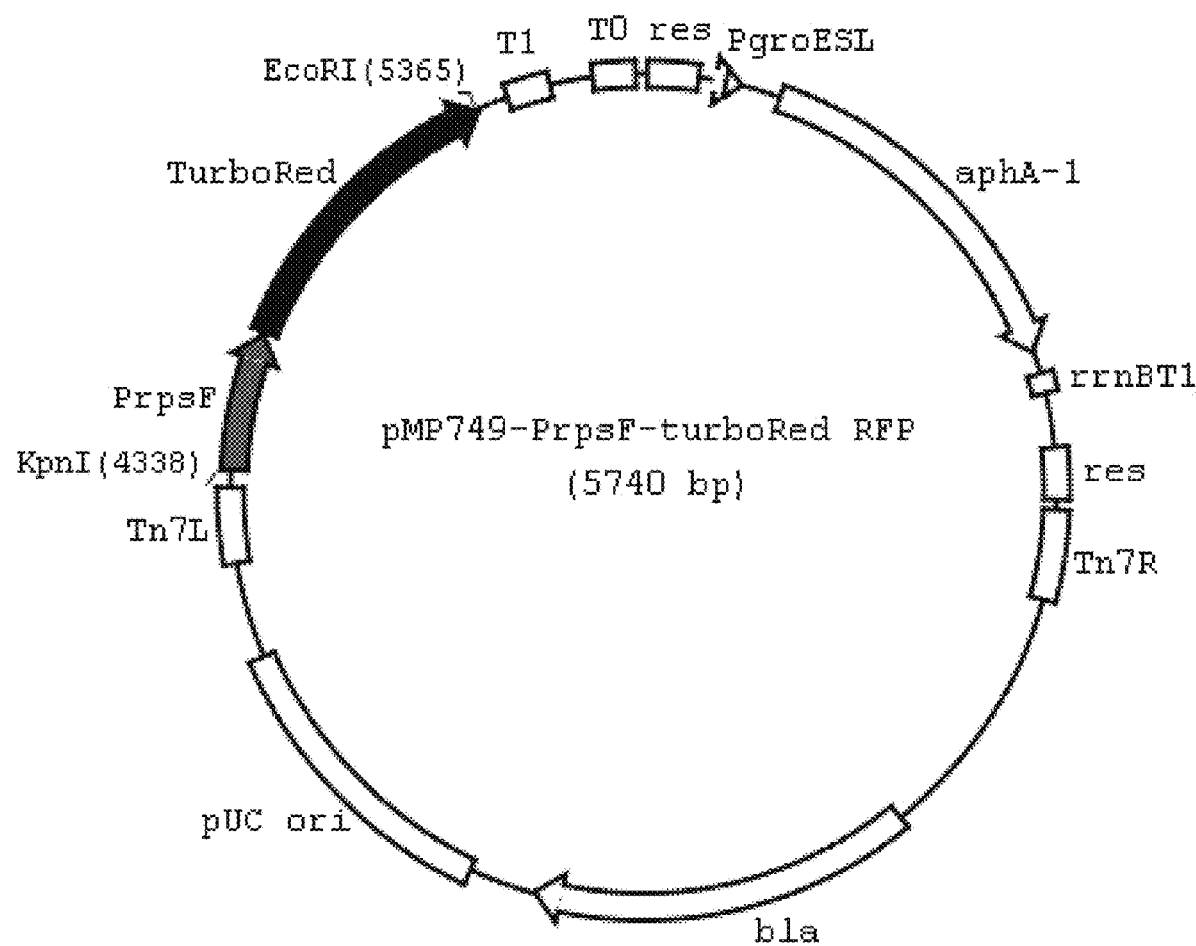

FIG. 8A shows a schematic representation of the plasmid pMP729 vector. FIG. 8B shows a schematic representation of the plasmid pMP749-prpsF-GFP vector. FIG. 8C shows schematic a representation of the plasmid pMP749-prpsF-RFP vector.

Figure 9A:
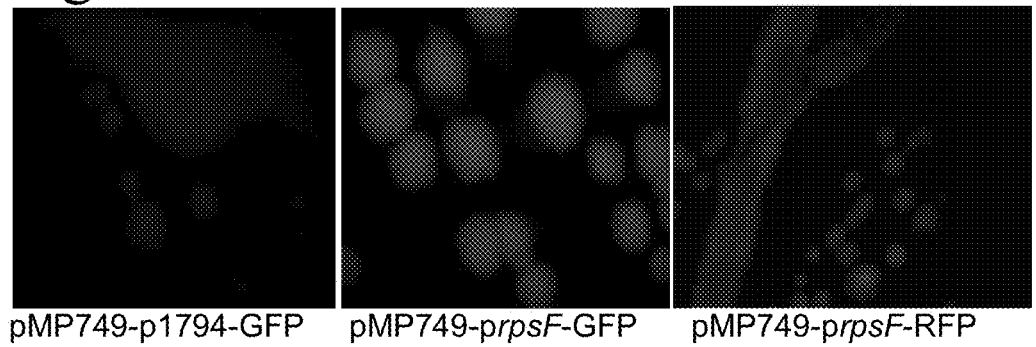
Figure 9B:
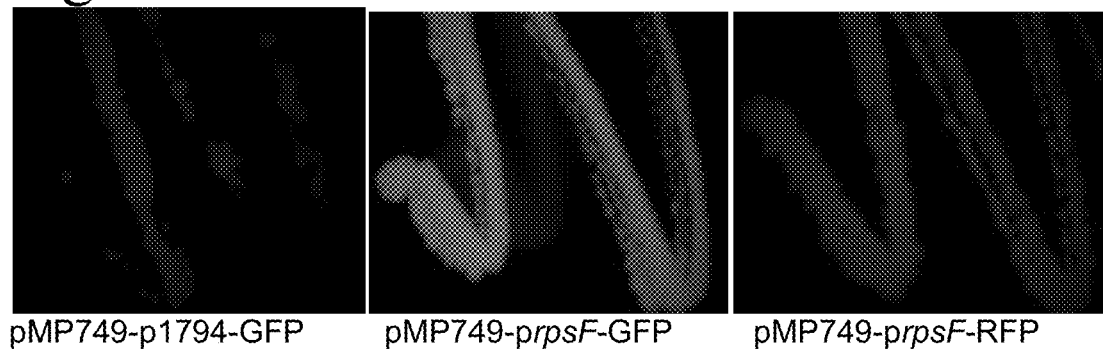
Figure 9C:
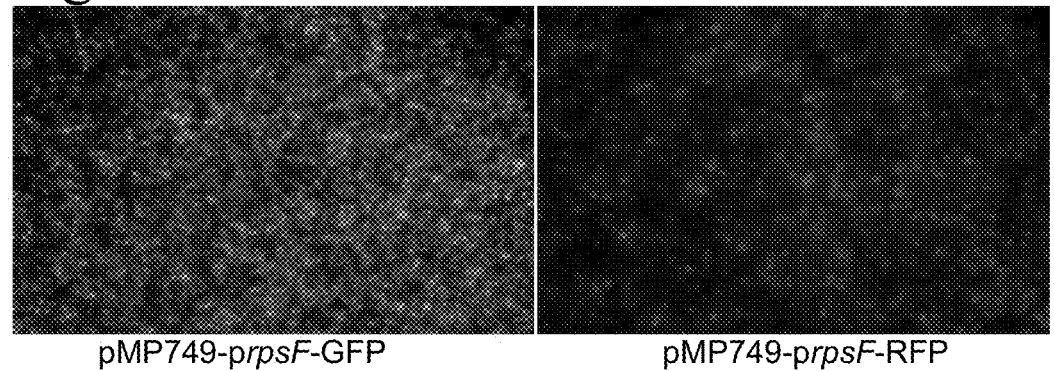

FIG. 9A shows fluorescence microscopy of *E. coli* DH5-α containing vector plasmid pMP749-prpsF-GFP and pMP749-prpsF-RFP. FIG. 9B shows fluorescence microscopy of *Francisella tularesis holarctica* LVS chromosomally integrated with vector plasmid pMP749-prpsF-GFP and pMP749-prpsF-RFP. FIG. 9C shows fluorescence microscopy of *Francisella tularesis* Schu S4 chromosomally integrated with vector plasmid pMP749-prpsF-GFP and pMP749-prpsF-RFP.

Figure 10A:
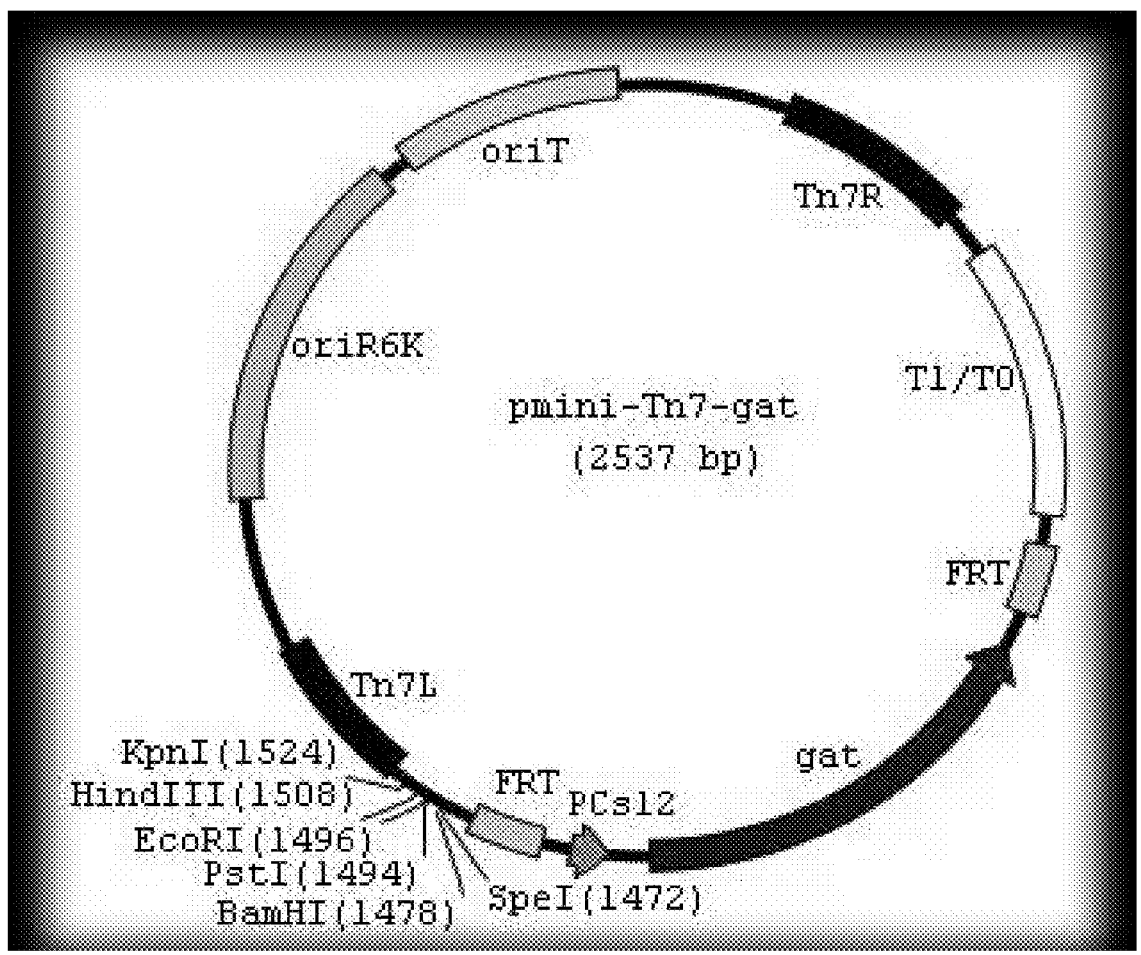
Figure 10B:
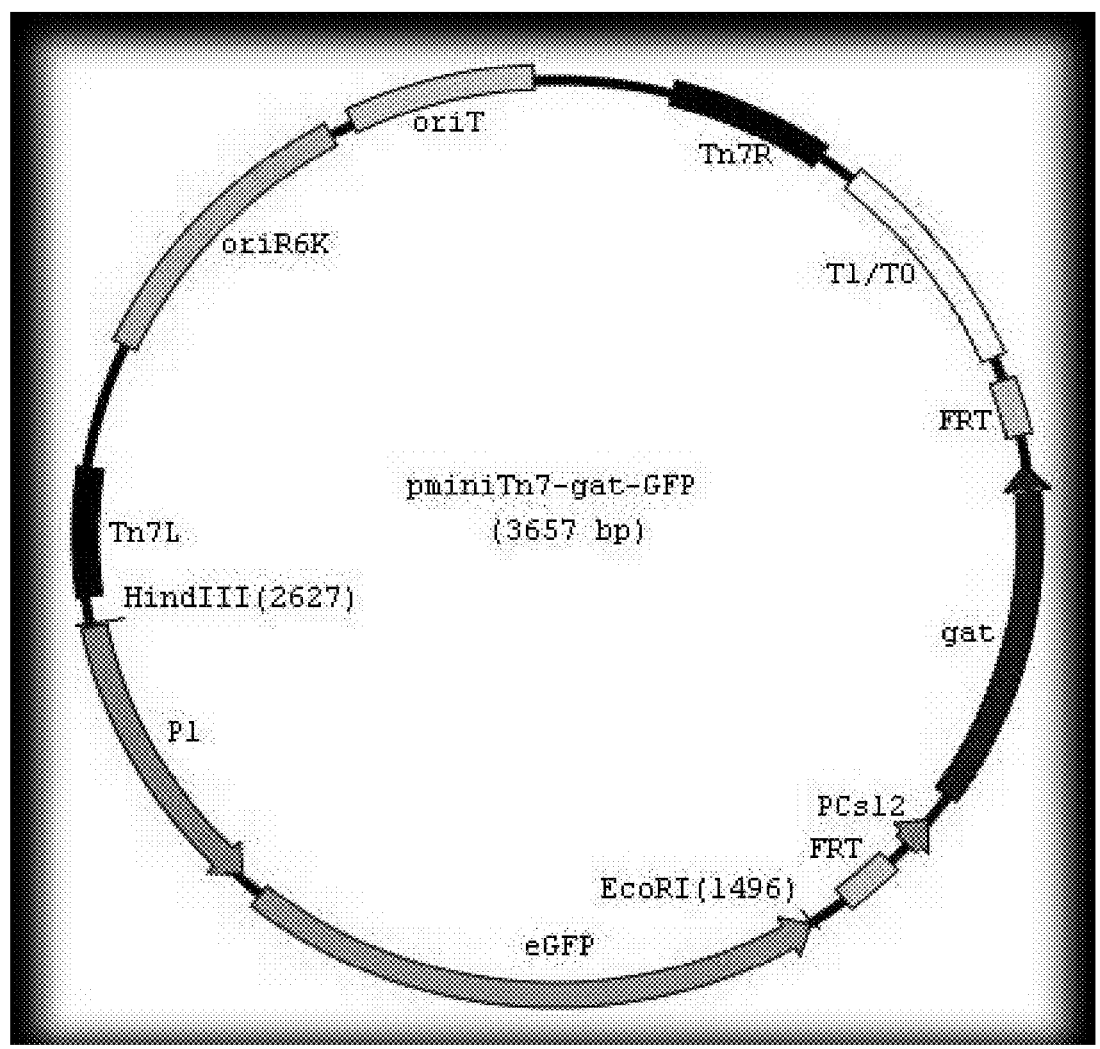
Figure 10C:
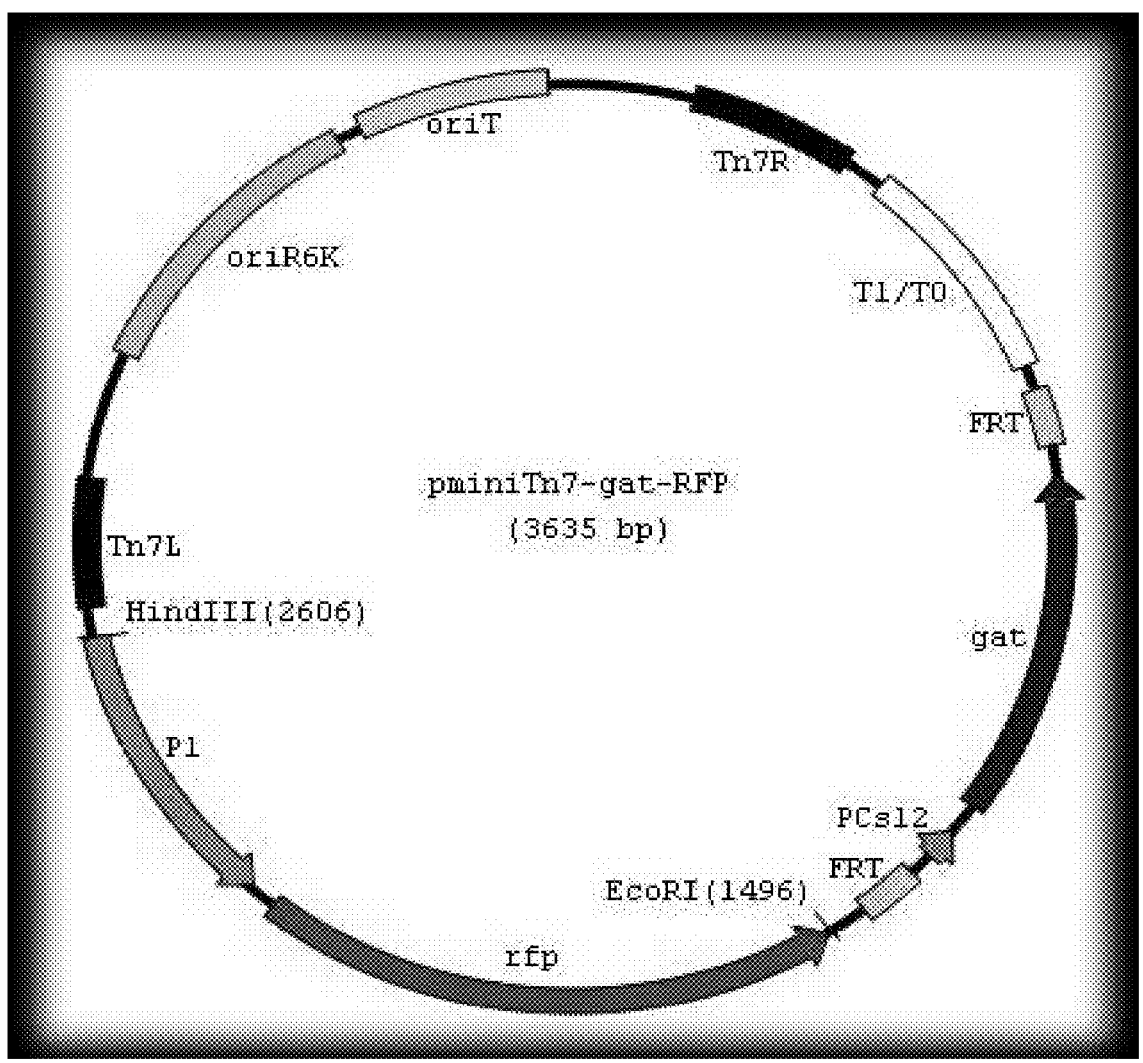

FIG. 10A shows a schematic representation of the plasmid pmini-Tn7-gat vector. FIG. 10B shows a schematic representation of the plasmid pmini-Tn7-gat-P1-GFP vector. FIG. 10C shows a schematic representation of the plasmid pmini-Tn7-gat-P1-RFP vector.

FIG. 11A shows *E. coli* E2071 harboring vector plasmid pmini-Tn7-gat-P1-GFP (top half of plate) and *E. coli* E2071 harboring vector plasmid pmini-Tn7-gat-P1-RFP (bottom half of plate) struck out on L-agar plates. FIG. 11B shows *Burkholderia thailandensis* chromosomally integrated with vector plasmid pmini-Tn7-gat-P1-GFP (top half of plate) and *Burkholderia thailandensis* chromosomally integrated with plasmid pmini-Tn7-gat-P1-RFP (bottom half of plate) struck out on L-agar plates. FIG. 11C shows fluorescence microscopy of the *E. coli* harboring plasmid pmini-Tn7-gat-P1-GFP (top square) and *E. coli* E2071 stable harboring plasmid pmini-Tn7-gat-P1-RFP (bottom square). FIG. 11D shows fluorescence microscopy of the *Burkholderia thaileensis* chromosomally integrated with vector plasmid pmini-Tn7-gat-P1-GFP (top square) and *Burkholderia thailandensis* chromosomally integrated with plasmid pmini-Tn7-gat-P1-RFP (bottom square).

FIG. 12A shows fluorescence microscopy of *Burkholderia thailandensis* chromosomally integrated with pmini-Tn7-gat-P1-GFP. FIG. 12B shows fluorescence microscopy of *Burkholderia thailandensis* chromosomally integrated with pmini-Tn7-gat-P1-RFP. FIG. 12C shows fluorescence microscopy of *Burkholderia mallei* chromosomally integrated with pmini-Tn7-gat-P1-GFP. FIG. 12D shows fluorescence microscopy of *Burkholderia pseudomallei* chromosomally integrated with pmini-Tn7-gat-P1-GFP. FIG. 12E shows fluorescence microscopy of *Burkholderia mallei* chromosomally integrated with pmini-Tn7-gat-P1-GFP within THP-1 macrophages.

DETAILED DESCRIPTION

Particular details of various embodiments of the invention are set forth to illustrate certain aspects and not to limit the scope of the invention. It will be apparent to one of ordinary skill in the art that modifications and variations are possible without departing from the scope of the embodiments defined in the appended claims. More specifically, although some aspects of embodiments of the present invention may be identified herein as preferred or particularly advantageous, it is contemplated that the embodiments of the present invention are not necessarily limited to these preferred aspects.

Unless defined otherwise, all technical and scientific terms used herein have the same meaning as commonly understood by one of ordinary skill in the art to which the presently-disclosed subject matter belongs.

In some embodiments of the presently-disclosed subject matter, a method of screening candidate compounds for possessing anti-bacterial efficacy suitable for rapid response to contamination by a bacterial pathogen is provided. In certain embodiments, the method comprises providing a modified bacterial pathogen, wherein the modification comprises a vector plasmid insert. The vector plasmid insert is engineered to constitutively express a chromosomal transcriptional fusion fluorescent protein that results in sustained fluorescence while the modified bacterial pathogen is alive. The method further comprises contacting a candidate compound with the modified bacterial pathogen, and subsequently determining whether the modified bacterial pathogen exhibits fluorescence. Candidate compounds are identified as comprising anti-bacterial efficacy where the fluorescence is extinguished.

In some embodiments of a method of screening candidate compounds for possessing anti-bacterial efficacy suitable for rapid response to contamination by a bacterial pathogen, the step of providing a modified bacterial pathogen comprises producing a modified bacterial pathogen, wherein the modification comprises a vector plasmid insert. The vector plasmid insert is engineered to constitutively express a chromosomal transcriptional fusion fluorescent protein that results in sustained fluorescence while the modified bacterial pathogen is alive.

In some embodiments of a method of screening candidate compounds for possessing anti-bacterial efficacy suitable for rapid response to contamination by a bacterial pathogen, the method comprises a high throughput screening method. In certain embodiments employing a high throughput screening method, the step of identification requires less than 200 ms.

In some embodiments of a method of screening candidate compounds for possessing anti-bacterial efficacy suitable for rapid response to contamination by a bacterial pathogen, the contamination by a bacterial pathogen results from intentional dissemination of the bacterial pathogen. In certain embodiments, the intentional dissemination of the bacterial pathogen results from bioterrorism. The CDC defines bioterrorism as the deliberate release of viruses, bacteria, or other germs (agents) used to cause illness or death in people, animals, or plants.

In some embodiments of a method of screening candidate compounds for possessing anti-bacterial efficacy suitable for rapid response to contamination by a bacterial pathogen, the chromosomal transcriptional fusion fluorescent protein is selected from the group consisting of optimized Green Fluorescent Protein (GFP) and optimized Red Fluorescent Protein (RFP). A 720-bp optimized GFP gene, Superfolder GFP, and a 699-bp optimized RFP gene, TurboRed RFP (GenScript), were utilized in certain preferred embodiments, as described in the Examples section under Methods (DNA manipulations). Those of skill in the art will recognize that modifications of the optimized GFP and optimized RFP proteins other than that provided in commercially available products may be utilized in the practice of the present invention. For example, other mutations of GFP or RFP that differ in excitation and emission characteristics, or any suitable form of GFP or RFP, or other fluorescent proteins, may be used in the practice of the present invention.

In some embodiments of a method of screening candidate compounds for possessing anti-bacterial efficacy suitable for rapid response to contamination by a bacterial pathogen, the bacterial pathogen comprises Category A, B, or C bacterial pathogens. (niaid.nih.gov/topics/BiodefenseRelated/Biodefense/Documents/category_a_progress_report.pdf; niaid.nih.gov/topics/BiodefenseRelated/Biodefense/Documents/categorybandc.pdf). Category A bacterial pathogens are defined by the CDC as high-priority agents that pose a risk to national security because they can be easily disseminated or transmitted from person to person, result in high mortality rates and have the potential for major public health impact, might cause public panic and social disruption, and require special action for public health preparedness. Category B bacterial pathogens are defined by the CDC as the second highest priority agents and include those bacterial pathogens that are moderately easy to disseminate, result in moderate morbidity rates and low mortality rates, and require specific enhancements of CDC's diagnostic capacity and enhanced disease surveillance. Category C bacterial pathogens are defined by the CDC as the third highest priority agents and include emerging pathogens that could be engineered for mass dissemination in the future because of availability, ease of production and dissemination, and potential for high morbidity and mortality rates and major health impact.

In certain embodiments, the Category A bacterial pathogen is selected from the group consisting of *Bacillus anthracis*, *Yersinia pestis*, and *Francilla tularensis*. In more particular embodiments, the bacterial pathogen *Bacillus anthracis* is selected from the group consisting of *Bacillus anthracis* Ames and *Bacillus anthracis* Stern. In even more particular embodiments, the vector plasmid insert is selected from the group consisting of pBJKΔBla1-p0253-GFP, pBJKΔBla1-p0253-RFP, pBKJΔBla1-pntr-GFP, pBKJΔBla1-pntr-RFP, pRP1028ΔBla1-p0253-GFP, and pRP1028ΔBla1-p0253-RFP. The vector plasmid inserts pBJKΔBla1-p0253-GFP, pBJKΔBla1-p0253-RFP, pBKJΔBla1-pntr-GFP, pBKJΔBla1-pntr-RFP, pRP1028ΔBla1-p0253-GFP, and pRP1028ΔBla1-p0253-RFP utilized in preferred embodiments of the present invention are those which are described in the Examples section under Methods (DNA manipulations; *Bacillus anthracis* plasmid construction). A biological material deposit of pBJKΔBla1-p0253-GFP (ATCC® Patent Deposit Designation PTA-126041), pBJKΔBla1-p0253-RFP (ATCC® Patent Deposit Designation PTA-126043), pBKJΔBla1-pntr-GFP (ATCC® Patent Deposit Designation PTA-126044), and pBKJΔBla1-pntr-RFP (ATCC® Patent Deposit Designation PTA-126042) was made on Sep. 10, 2019 with the American Type Culture Collection (ATCC®), P.O. Box 1549, Manassas, Va., 20108, USA.

In other particular embodiments, the bacterial pathogen *Yersinia pestis* is selected from the group consisting of *Yersinia pestis* CO92 *Yersinia pestis pseudotuberculosis*. In even more particular embodiments, the vector plasmid insert is selected from the group consisting of pUC18-R6KT-mini-Tn7T-Km-2pcysZK-GFP and pUC18-R6KT-mini-Tn7T-Km-2pcysZK-RFP. The vector plasmid inserts pUC18-R6KT-mini-Tn7T-Km-2pcysZK-GFP and pUC18-R6KT-mini-Tn7T-Km-2pcysZK-RFP utilized in preferred embodiments of the present invention are those which are described in the Examples section under Methods (DNA manipulations; *Yersinia* plasmid construction).

In some particular embodiments, the bacterial pathogen *Francisella tularesis* is selected from the group consisting of *Francisella tularesis* Schu S4 and *Francisella tulareiss holaractica* LVS. In even more particular embodiments, the vector plasmid insert is selected from the group consisting of pMP749-prpsF-GFP, pMP749-prpsF-RFP, pMP749-p1794-GFP, and pMP749-p1749-RFP. The vector plasmid inserts pMP749-prpsF-GFP, pMP749-prpsF-RFP, pMP749-p1794-GFP, and pMP749-p1749-RFP utilized in preferred embodiments of the present invention are those which are described in the Examples section under Methods (DNA manipulations; *Francisella tularensis* plasmid construction).

In certain embodiments, the Category B bacterial pathogen is *Burkholderia*. In more particular embodiments, the bacterial pathogen *Burkholderia* is selected from the group consisting of *Burkholderia mallei*, *Burkholderia pseudomallei*, and *Burkholderia thailandensis*. In even more particular embodiments, the plasmid insert is the vector plasmid insert is selected from the group consisting of pmini-Tn7-gat-P1-GFP and pmini-Tn7-gat-P1-RFP. The vector plasmid inserts pmini-Tn7-gat-P1-GFP and pmini-Tn7-gat-P1-RFP utilized in preferred embodiments of the present invention are those which are described in the Examples section under Methods (DNA manipulations; *Burkholderia* plasmid construction).

In other embodiments of the presently-disclosed subject matter, a *Bacillus anthracis* cell genetically engineered with a vector plasmid insert to constitutively express a chromosomal transcriptional fusion fluorescent protein is provide. The vector plasmid insert is selected from the group consisting of pBJKΔBla1-p0253-GFP, pBJKΔBla1-p0253-RFP, pBKJΔBla1-pntr-GFP, pBKJΔBla1-pntr-RFP, pRP1028ΔBla1-p0253-GFP, and pRP1028ΔBla1-p0253-GFP (described in the Examples section under Methods (DNA manipulations; *Bacillus anthracis* plasmid construction)). In more particular embodiments, the *Bacillus anthracis* is selected from the group consisting of *Bacillus anthracis* Ames and *Bacillus anthracis* Stern.

In additional embodiments of the presently-disclosed subject matter, *Yersina pestis* cell genetically engineered with a vector plasmid insert to constitutively express a chromosomal transcriptional fusion fluorescent protein is provided. The vector plasmid insert is selected from the group consisting of pUC18-R6KT-mini-Tn7T-Km-2pcysZK-GFP and pUC18-R6KT-mini-Tn7T-Km-2pcysZK-GFP (described in the Examples section under Methods (DNA manipulations; *Yersinia* plasmid construction)). In more particular embodiments, the *Yersinia pestis* is selected from the group consisting of *Yersinia pestis* CO92 and *Yersinia pseudotuberculosis*.

In some embodiments of the presently-disclosed subject matter, a *Francisella tularesis* cell genetically engineered with a vector plasmid insert to constitutively express a chromosomal transcriptional fusion fluorescent protein is provided. The vector plasmid insert is selected from the group consisting of pMP749-prpsF-GFP, pMP749-prpsF-RFP, pMP749-p1794-GFP, and pMP749-p1749-RFP (described in the Examples section under Methods (DNA manipulations; *Francisella tularensis* plasmid construction)). In more particular embodiments, the *Francisella tularesis* is selected from the group consisting of *Francisella tularesis* Schu S4 and *Francisella tularesis holarctica* LVS.

In further embodiments of the presently-disclosed subject matter, a *Burkholderia* cell genetically engineered with a vector plasmid insert to constitutively express a chromosomal transcriptional fusion fluorescent protein is provided. The vector plasmid insert is selected from the group consisting of pmini-Tn7-gat-P1-GFP and pmini-Tn7-gat-P1-RFP (described in the Examples section under Methods (DNA manipulations; *Burkholderia* plasmid construction)). In more particular embodiments, the *Burkholderia* is selected from the group consisting of *Burkholderia mallei*, *Burkholderia pseudomallei*, and *Burkholderia thailandensis*.

The vector plasmid inserts used in the disclosed preferred embodiments of the present invention are those that are described in the Examples section under Methods (DNA manipulations). However, it will be readily comprehended by those of skill in the art that the disclosed vector plasmid inserts can be modified in several ways within the scope of this invention. Such modifications can include, for example, inserting other potential genes of interest or genetic based signals to direct or target the vector to cells of interest. Further modifications include using other constitutive or highly expressed Bacillus sp., Yersinia sp., Francisella tularensis sp., and Burkholderia sp. promoters that will also allow for stable, constitutively expressed chromosomal transcriptional GFP and RFP reporters in these Category A, B, or C bacterial pathogens. (Su et al. *Characterization of stable, constitutively expressed, chromosomal green and red fluorescent transcriptional fusions in the select agent bacterium, Francisella tularensis Shu S4 and the surrogate type B live vaccine strain (LVS)*. Applied Microbiology Biotechnology (2013) 97:9029-9041. Zaide et al., *Identification and Characterization of Novel and Potent Transcription Promoters of Francisella tularensis*. Applied and Environmental Microbioloy, (2011) 77: 1608-1618.) The techniques necessary to manipulate the preferred embodiments of the vector plasmid inserts and cloned genes to carry out such modifications are well known to those of skill in the art. Additionally, in preferred embodiments of the present invention, vector plasmid inserts were introduced into *E. coli* by $CaCl_2$-mediated transformation and into *Bacillus* sp., *Yersinia* sp., *Francisella tularensis* sp., and *Burkholderia* sp. by electroporation or conjugation. However, it will be readily understood by those of skill in the art that other means of transfection may be utilized in the practice of the present invention. For example, transfection may be accomplished with by other chemical or electrical means.

The cell lines of the present invention can be used in may lines of investigation in which it is desirable to monitor cell death. For example, the disclosed cell lines have potential applications in high-throughput screening of compounds for identifying potential therapeutics to the strains. Additionally, the disclosed cell lines have potential to be used in virulence studies, for the testing of vaccine candidates, for in vivo animal models, infective indices experiments, intramacrophage survival studies, and siRNA screening.

In additional embodiments of the presently-disclosed subject matter, a method of responding to intentional bioterrorist dissemination of a known or unknown bacterial pathogen is provided. In certain embodiments, the method comprises isolating a sample cell of the bacterial agent and modifying the cell by inserting a vector plasmid engineered to constitutively express a chromosomal transcriptional fusion fluorescent protein that results in sustained fluorescence while the modified bacterial pathogen is alive. The method further comprises screening a library of anti-bacterial agents for efficacy against the known or unknown bacterial pathogen. Screening comprising the steps of contacting a candidate compound with the modified bacterial pathogen and determining whether the modified bacterial pathogen exhibits fluorescence. Screening further comprises identifying a candidate compound as comprising anti-bacterial efficacy against the known or unknown bacterial agent where the fluorescence is extinguished, and treating the contamination with the identified antibacterial compound.

EXAMPLES

Methods

Bacterial Strains, Growth Media and Plasmids

Bacterial strains used in this study are listed in Table 1. The plasmid vectors used in this study are listed in Table 2. All cloning was conducted in *Escherichia coli* DH5α or EPmax10B (Bio-Rad). *E. coli* was routinely grown at 37° C. in Luria-Bertani Broth (LB, Life Technologies) or 1×M9 minimal medium plus 20 mM glucose (MG medium). All work with the type A virulent strains *Bacillus anthracis* Ames, *Yersinia pestis* CO92, *Francisella tularensis* Schu S4, *Burkholderia pseudomallei* K96243, *Burkholderia mallei* NBL7 and their derivatives were performed in a biosafety level 3 (BSL-3) facility using BSL-3 practices, procedures and containment equipment. The surrogate strains of the aforementioned select agents were *Bacillus anthracis* Sterne, *Yersinia pseudotuberculosis* (ATCC 11960), *Francisella tularensis holarctica* LVS, and *Burkholderia thailandensis* (ATCC 700388), respectively. *Bacillus anthracis* sp. and their derivatives were grown aerobically at 37° C. in brain heart infusion (BHI) medium (Difco). *Yersinia pseudotuberculosis, Yersinia pestis*, and their derivatives were cultured aerobically at 37° C. in typtic soy broth (TSB) (Difco). *Francisella tularensis holarctica* LVS and *Francisella tularensis* Schu S4 were grown aerobically at 37° C. in tryptic soy broth (TSB) supplemented with 0.1% cysteine, or on chocolate agar. *Burkholderia thailandensis, Burkholderia pseudomallei, Burkholderia mallei*, and their derivatives were grown at 37° C. in LB both or MG medium. Antibiotics and nonantibiotic antibacterial compound were added at the following concentrations when required: for *E. coli* strains, kanamycin, 50 μg/ml; ampicillin, 100 μg/ml; erythromycin, 300 μg/ml; and glyphosate (GS), 0.3%; for *Bacillus anthracis*, erythromycin, 5 μg/ml; tetracycline, 10 μg/ml; and kanamycin, 20 μg/ml; for *Yersinia pseudotuberculosis* and *Yersinia pestis*, kanamycin, 20 μg/ml; chloramphenicol, 35 μg/ml; for *Francisella tularensis*, kanamycin, 10 μg/ml; ampicillin, 50 μg/ml; and nourseothricin, 50 μg/ml; for *Burkholderia thailandensis*, GS, 0.04%; for *Burkholderia pseudomallei*, GS, 0.3%; for *Burkholderia mallei*, GS, 0.2%.

TABLE 1

| Pathogen | Fluorescent protein | Promoter | Vector |
|---|---|---|---|
| *Bacillus anthracis* | Optimized GFP<br>Optimized RFP | p0253, pntr | pBKJ258, pRP1028, pRP1028-rfp |
| *Francisella tularensis* | Optimized GFP<br>Optimized RFP | prpsF | pMP815, pMP749 |
| *Yersinia pestis* | Optimized GFP<br>Optimized RFP | Two copies of pcysZK | pUC18R6KT-mini-Tn7-Km |
| *Burkholderia mallei* | Optimized GFP<br>Optimized RFP | P1 | Pmini-Tn7-gat |
| *Burkholderia pseudomallei* | Optimized GFP<br>Optimized RFP | P1 | Pmini-Tn7-gat |

TABLE 2

| Pathogens | Surrogates | Virulent Strains |
|---|---|---|
| Bacillus anthracis | Bacillus anthracis Sterne - Colorado Serum Company Anthrax Spore Vaccine 19102 | NR411 Bacillus anthracis Ames |
| Francisella tularensis | Francisella tularensis holarctica LVS Francisella novicida - NR-13 | NR643 Francisella tularensis Type A Schu S4 |
| Yersinia pestis | Yersinia pseudotuberculosis - ATCC# 11960 | NR641 Yersinia pestis Biovar Orientalis strain CO92 |
| Burkholderia mallei | Burkholderia thailandensis - ATCC #700388 | NR23 Burkholderia mallei NBL 7 |
| Burkholderia pseudomallei | Burkholderia thailandensis - ATCC #700388 | NR4073 Burkholderia pseudomallei strain K96243 |

DNA Manipulations

Genomic DNA isolation, PCR, restriction enzyme digestion, ligation, cloning and DNA electrophoresis were done according to standard techniques (Maniatis T., et al. (1982). *Molecular cloning: a laboratory manual*. Cold Spring Harbor Laboratory, Cold Spring Harbor). All oligonucleotide primers were synthesized by Integrated DNA Technologies (IDT). PCR was performed using either Choice Taq Mastermix (Denville Scientific, Inc.) or Pfu DNA polymerase (Strategene). Plasmids were prepared using a QIAprep Spin miniprep kits (QIAGEN) as recommended by the manufacturer. DNA fragments were purified using either a QIAquick PCR purification kit (QIAGEN) or a QIAquick gel extraction kit (QIAGEN). All cloned inserts were confirmed by automated DNA sequencing performed at the DNA Core Facility of the Cincinnati Children's Hospital Medical Center. Plasmids were introduced into *E. coli* by $CaCl_2$-mediated transformation and into *Bacillus* sp., *Yersinia* sp., *Francisella tularensis* sp., and *Burkholderia* sp. by electroporation or conjugation.

Reporter Plasmid Construction

A 720-bp optimized GFP gene, Superfolder GFP, and a 699-bp optimized RFP gene, TurboRed RFP (GenScript), were first amplified by PCR with pair of primers GFP/Pst5' and GFP/ApaI 3', and pair of primers RFP/Pst5' and RFP/Eco3', respectively. The PCR products superfolder GFP and turboRed RFP were cut with the restriction enzymes indicated in the primer names and fused to bioinformatically chosen promoters. A bioinformatic approach (see below) was used to identify (i) highly and (ii) constitutively expressed genes both in vitro and in vivo (e.g., during intra-macrophage survival). Genomic DNA from the various *Bacillus* sp., *Yersinia* sp., *Francisella tularensis* sp., and *Burkholderia* sp. strains were used as a template to amplify the desired promoters by PCR.

Bacillus anthracis Plasmid Construction

Figure 1B:
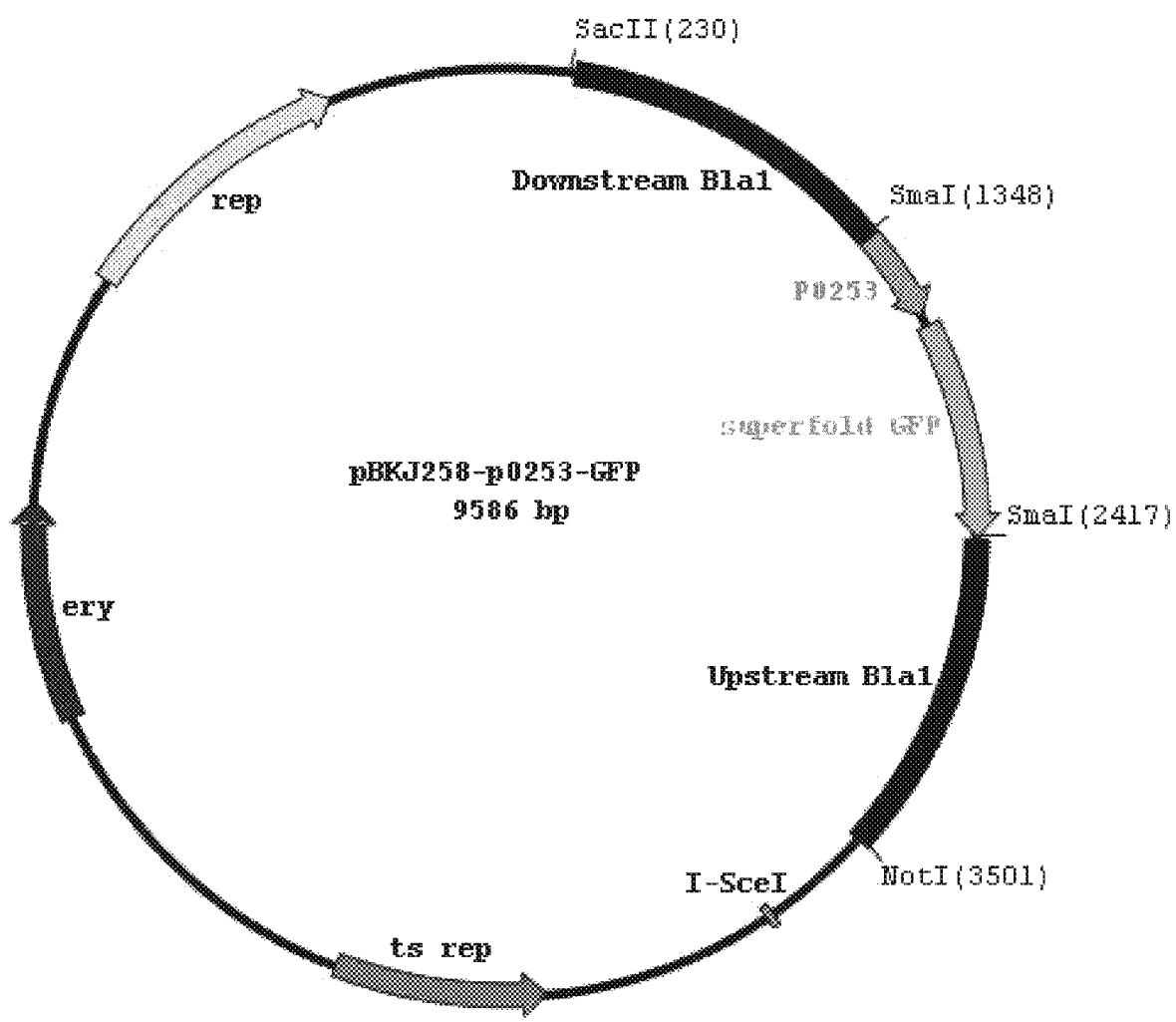
Figure 1C:
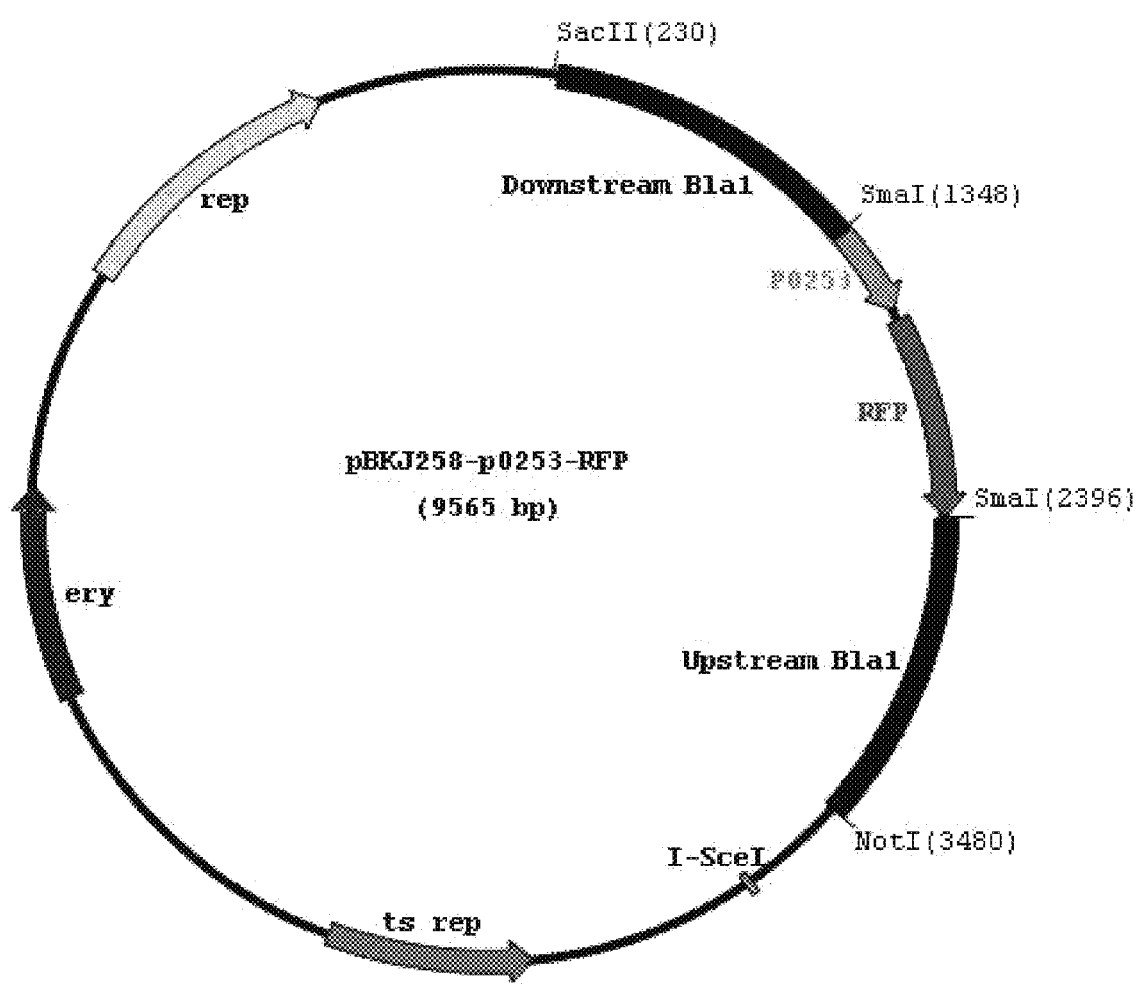
Figure 2A:
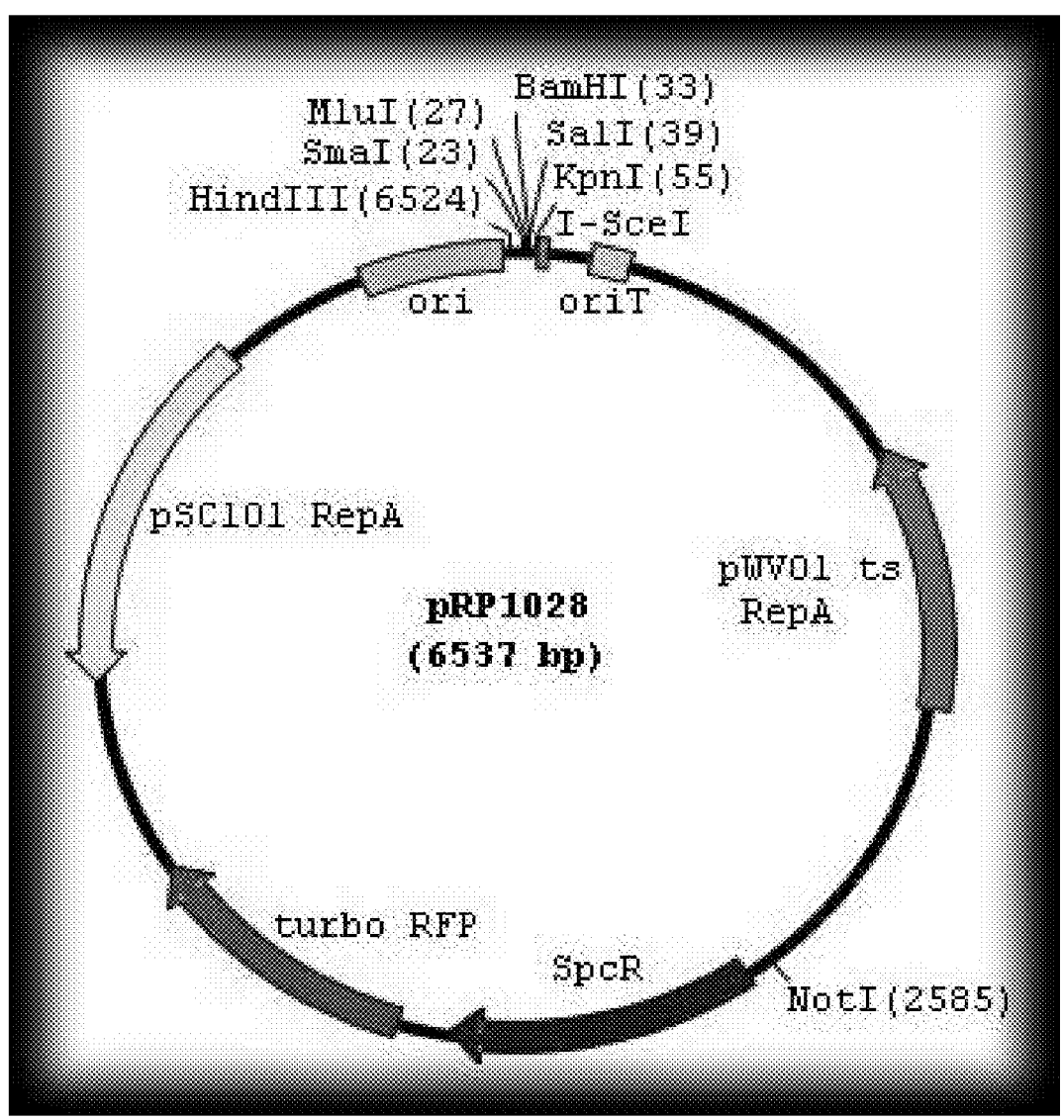
Figure 2B:
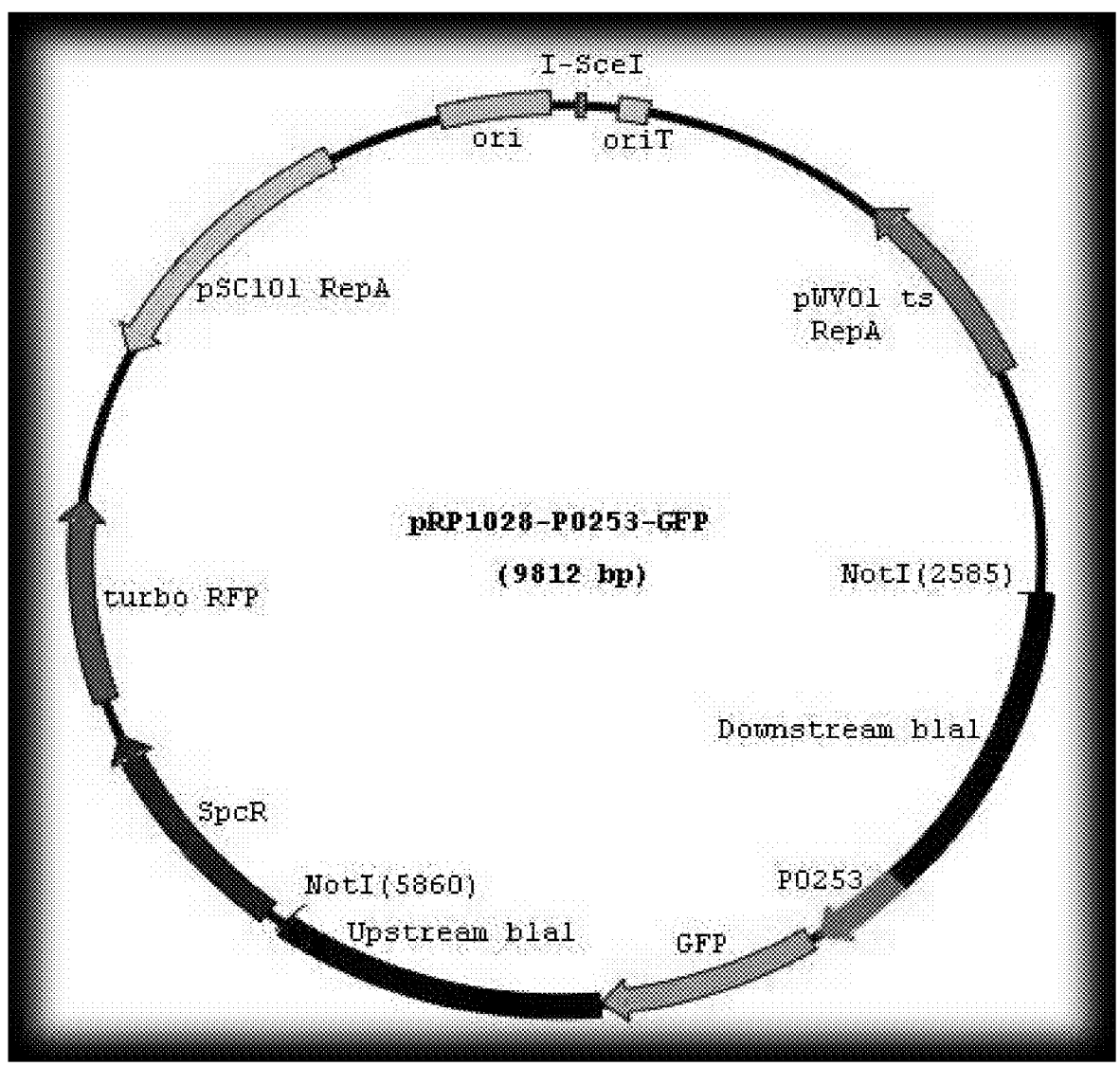
Figure 2C:
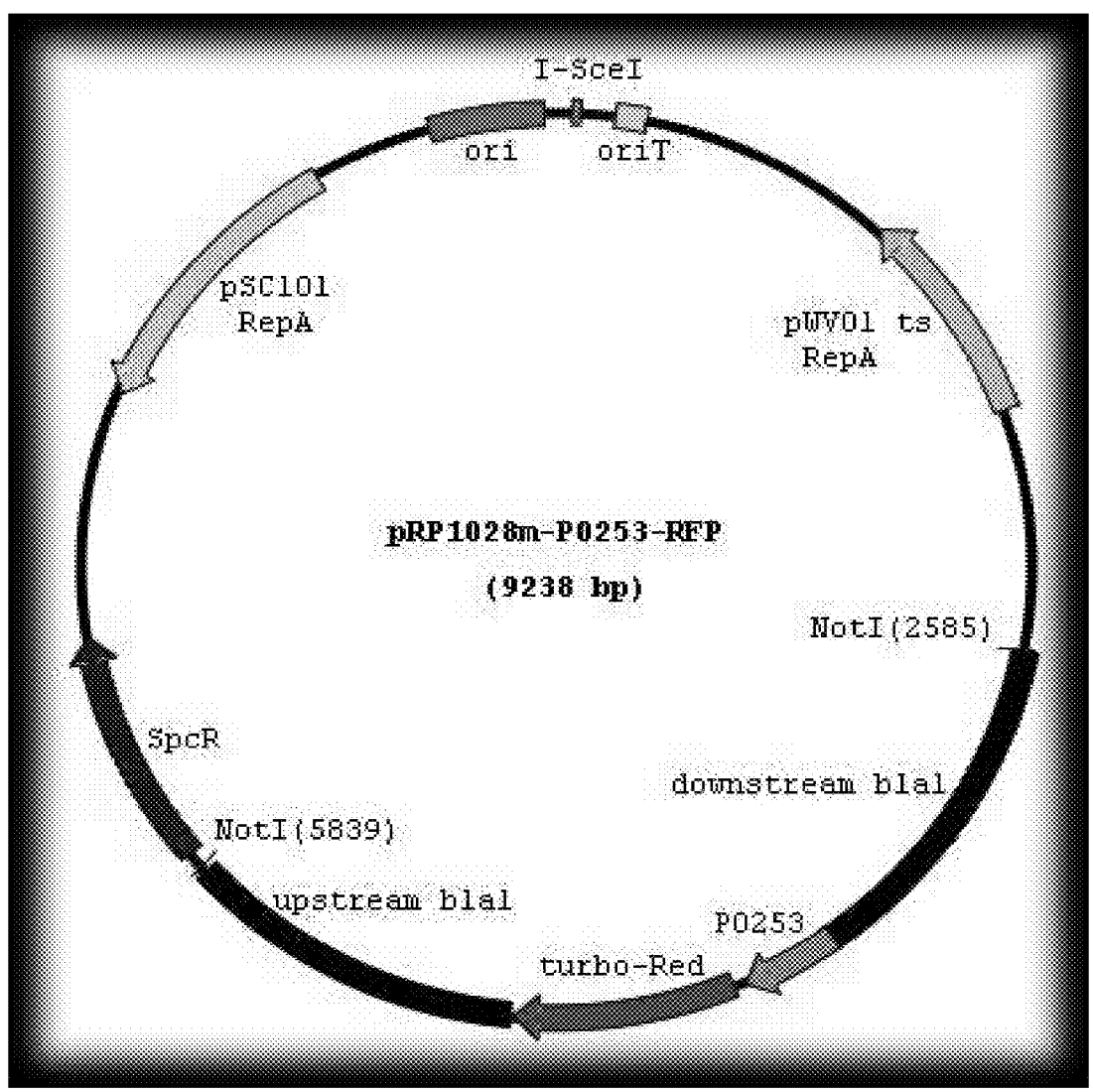

The bla1 gene fragments were cloned 1 kb upstream and 1 kb downstream between NotI and SacII sites of the integration vector pBKJ258, creating pBKJΔBla1. The p0253 promoter (or pntr promoter)-driven superfolder GFP or TurboRed RFP were then inserted into unique smaI site pBKJΔBla1, creating constructs pBKJΔBla1-pntr-GFP, pBKJΔBla1-pntr-RFP, pBKJΔBla1-p0253-GFP, and pBKJΔBla1-p0253-RFP (FIG. 1). All vector plasmids were confirmed by sequencing. The p0253 (or pntr) promoter-driven vector plasmids were integrated into bla1 gene in *Bacillus anthracis* Sterne, and into *Bacillus anthracis* Ames with vector plasmids pRP1028ΔBla1-p0253-GFP and pRP1028ΔBla1-p0253-RFP following standard protocol. (Janes B K et al., Routine markerless gene replacement in *Bacillus anthracis*. Infection and Immunity (2006) 1949-1953). The p0253 promoter-driven vector plasmids were used for the Ames strain. The erythromycin resistance marker in pBKJ258 was not appropriate for use in the Ames strain. The pRP1028 vector plasmid, which carries spectinomycin resistance as selectable marker, was modified by EcoRI and EcoOI091 restriction enzyme digestion to remove 552 bp turbo RFP internal fragment and created pRP1028-rfp. The 3,029 bp fragment ΔBla1-p0253-GFP or RFP was then cloned into the NotI unique site of pRP1028 and pRP1028-rfp, respectively; creating vector plasmids pRP1028ΔBla1-p0253-GFP, and pRP1028ΔBla1-p0253-RFP. Clones were confirmed by sequencing (FIG. 2) and introduced into the Ames strain. The chromosomally integrated Stern (FIG. 3) and Ames (FIG. 4) strains were validated by fluorescence microscope.

Yersinia Plasmid Construction

Figure 5A:
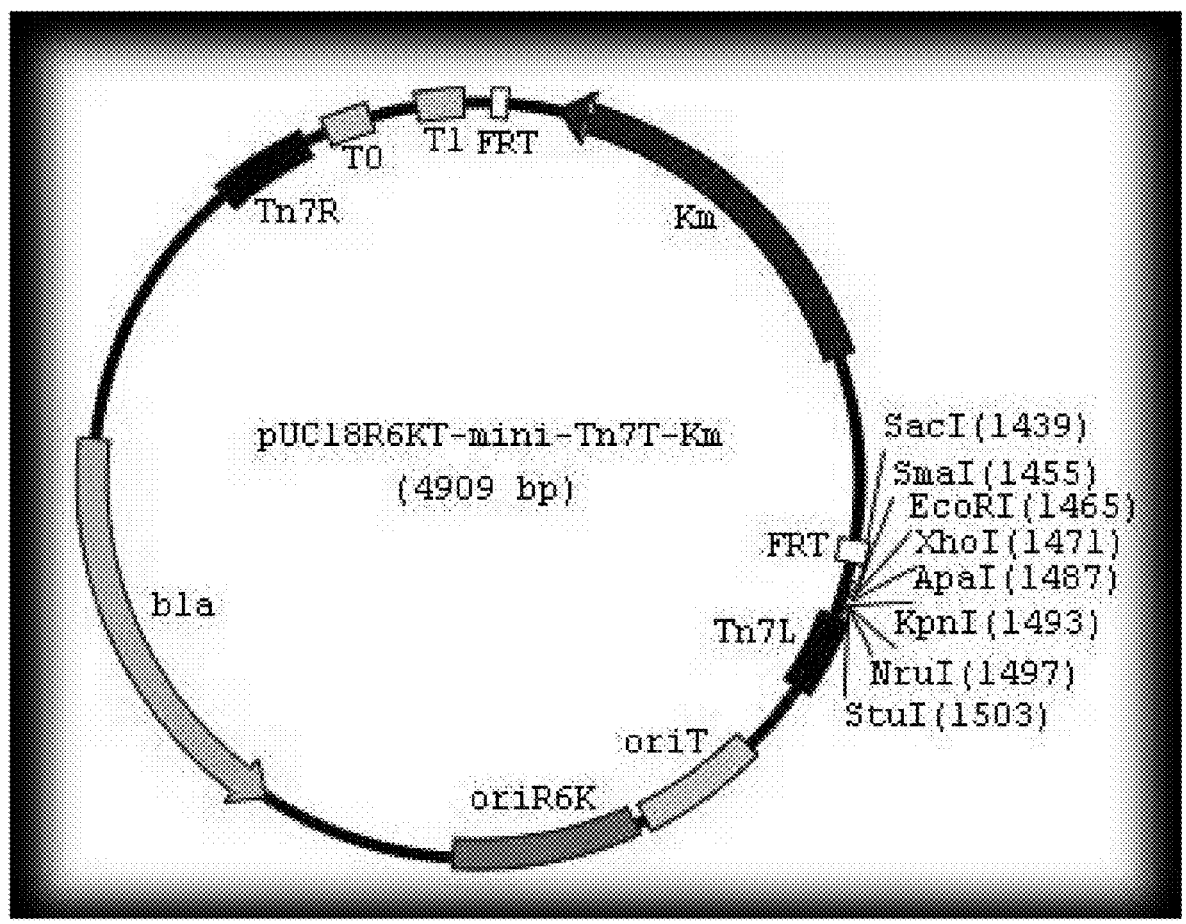
Figure 5B:
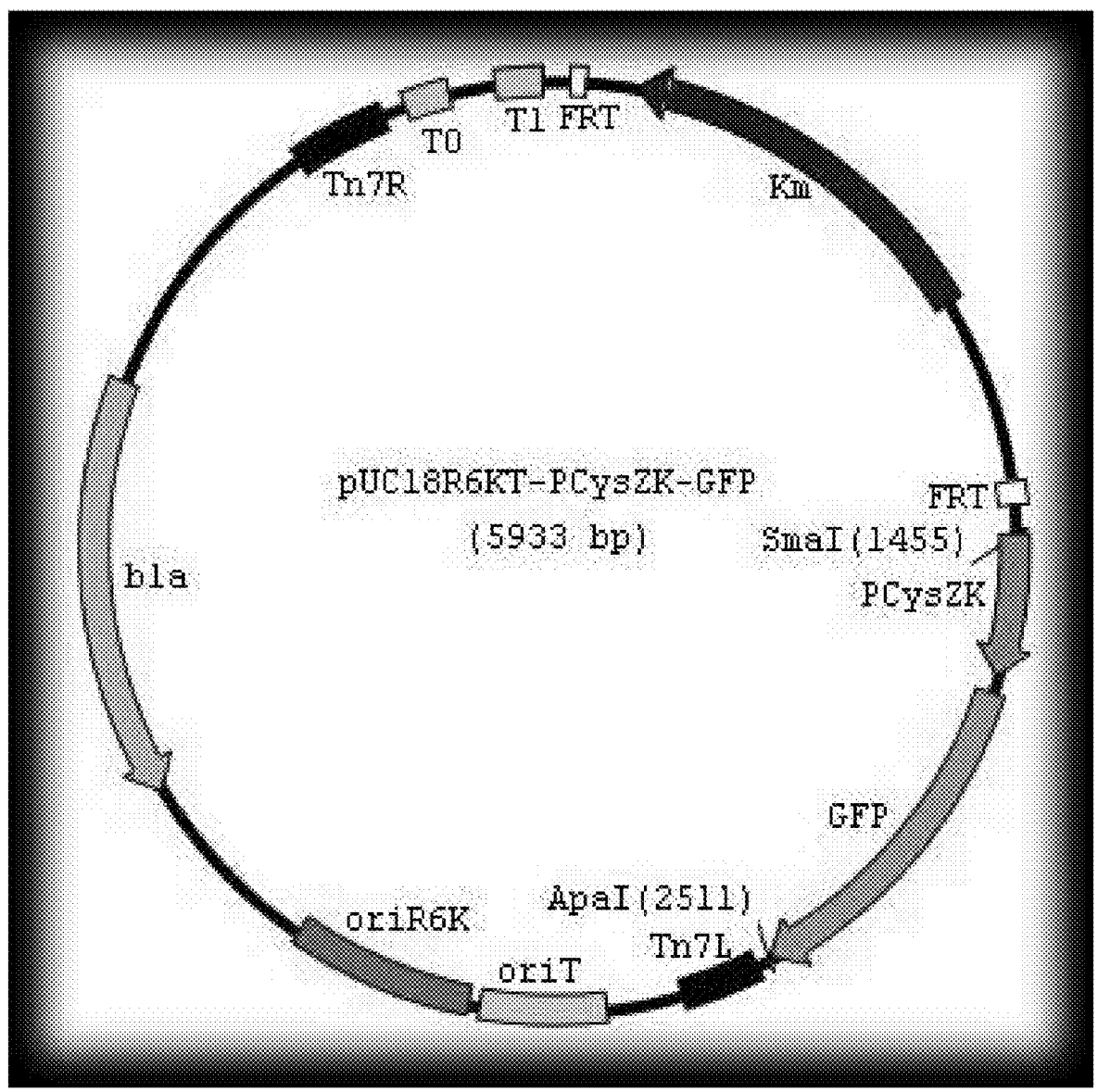
Figure 5C:
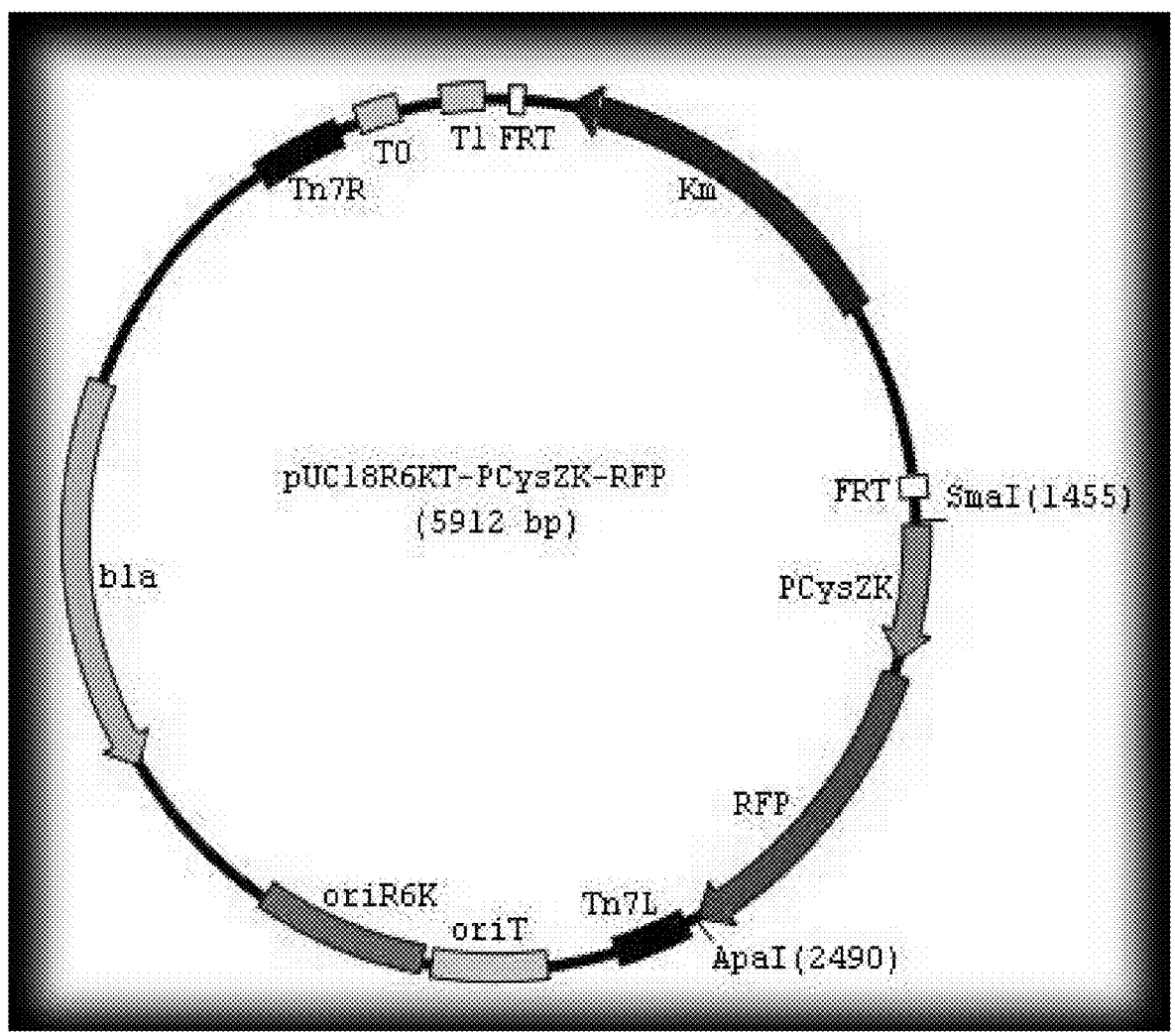
Figure 6A:
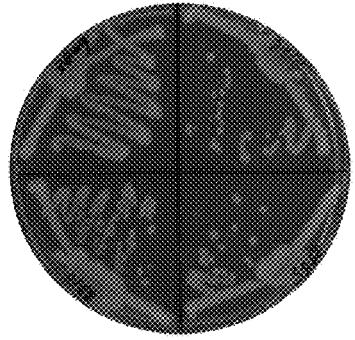
Figure 6B:
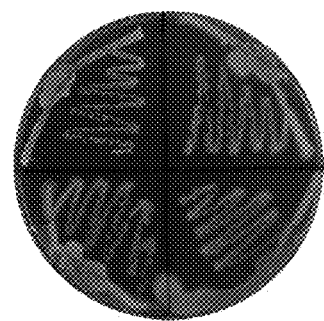
Figure 6C:
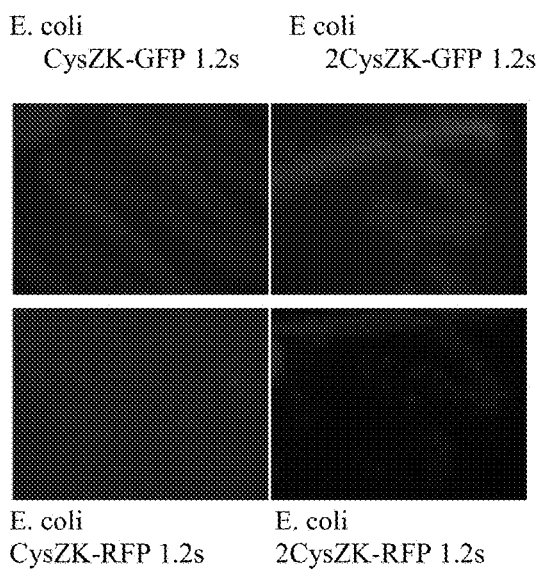
Figure 6D:
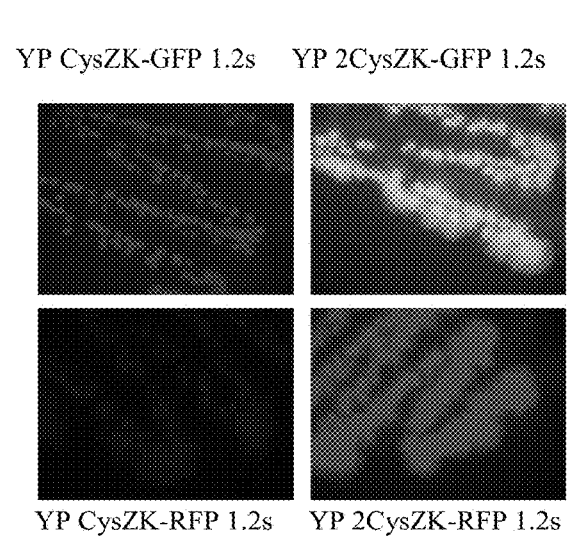

Yersinia promoter pcysZK was fused into enhanced GFP and RFP, and two copies of the fusions were first cloned between SmaI and ApaI sites, and then ApaI and KpnI sites of pUC18-R6KT-mini-Tn7T-Km in the same orientation, creating vector plasmids pUC18-R6KT-2pcysZK-GFP and pUC18-R6KT-2pcysZK-RFP, respectively (FIG. 5). (Choi, K H et al., *A Tn7-based broad-range bacterial cloning and expression system*. Nature Methods (2005) p. 443-448.) All vector plasmids were confirmed by sequencing. The vector plasmids were conjugated into *Yersinia pseudotuberculosis* and subsequently *Yersina pestis* CO92. The resultant chromosomally integrated strains were confirmed to fluoresce, and confirmed to have vector plasmid insertion at the Tn7 sites (FIGS. 6 & 7). The Km resistant marker was recycled by introducing plasmid pFLP2, which was then cured by sucrose counter selection. The genomic DNA of both the GFP- and RFP-tagged *Yersina pestis* CO92 was isolated. PCR analysis confirmed the correct vector plasmid insertion at Tn7 site and presence of three virulence plasmids.

Francisella tularensis Plasmid Construction

The Tn7 system was utilized. (LoVullo E. D. et al., *Single-copy chromosomal integration systems for Francisella tularensis*. Microbiology (2009) 155(Pt 4): pgs 1152-63). The TN7 system consists of an unstable transposase plasmid pMP720, a mini-Tn7 transposon vector pMP749 and a γδ-resolvase plasmid pMP672. The hyg gene of the plasmids pMP720 and pMP672 was replaced with the nat1 gene, which confers nourseothricin (protein synthesis inhibitor) resistance. To facilitate this, the plasmids pMP720 and pMP672 were first digested with NdeI and FseI to release a 637-bp 5' end of the hyg gene. Next, a 570-bp nat1 gene from pTZ559 (a gracious gift from Dr. T. Zahrt, Medical College of Wisconsin) was amplified by PCR and cloned between the NdeI and FseI sites of pMP720 and pMP672 which lacked the hyg genes, yielding pMP720-Nat1 and pMP672-Nat1). Next, the promoter p1794- or prpsF-driven GFP and RFP reporter fusions were cloned between KpnI and EcoRI sites of pMP749, creating vector plasmids pMP749-p1794-GFP (not shown), pMP749-prpsF-GFP, pMP749-p1794-RFP (not shown) and pMP749-prpsF-RFP (FIG. 8). A typical experimental procedure was then employed by first electroporating the transposase plasmid pMP720-Nat1 into the Schu S4 and LVS strains and selecting for hygromycin-resistant transformants. One hyg$^R$ transformant was then electroporated with the vector plasmids pMP749-p1794-GFP, pMP749-prpsF-GFP, pMP749-p1794-RFP, or pMP749-prpsF-RFP, respectively, and the transposon insertions were selected on media containing kanamycin. After curing the unstable plasmid pMP720-Nat1, the kanamycin marker was deleted from the Tn7 insertion strains by the introduction of the resolvase plasmid pMP672-Nat1. Finally, the pMP672-Nat1 plasmid was cured, and the Shu S4 and LVS with vector plasmid insertions at the attTn7 sites were confirmed by PCR analysis and DNA sequencing. *E. coli* DH5-α harboring plasmids pMP749-prpsF-GFP or pMP749-prpsF-RFP, or the *F. tularensis* LVS and Schu S4 strains carrying p1794- or prpsF-driven GFP and RFP vector plasmids integrated at the chromosomal attTn7 site were validated by fluorescence microscope (FIG. 9). The promoter prpsF is much stronger than the promoter p1794 as demonstrated by the brightness of fluorescence.

Burkholderia Plasmid Construction

Strong, constitutive and broad-host-range P1 integron promoter was fused to enhanced GFP and RFP, respectively. All reporter fusions were cloned between HindIII and EcoRI sites of pmini-Tn7-gat and confirmed by DNA sequencing, creating vector plasmids pmini-Tn7-gat-P1-GFP and pmini-Tn7-gat-P1-RFP (FIG. 10). These vector plasmids were delivered into surrogate *Burkholderia thailandensis* and subsequently *Burkholderia malli* NBL and *pseudomalli* strain K96243 genomes at Tn7 site via conjugation. (Norris, M. H. et al., *Glyphosate resistance as a novel select-agent-compliant, non-antibiotic-selectable marker in chromosomal mutagenesis of the essential genes asd and dapB of Burkholderia pseudomallei*. Applied and Environmental Microbiology (2009), p. 6062-6075, Vol. 75, No. 19). The chromosomally integrated *Burkholderia thailandensis*, *Burkholderia malli* NBL, and *pseudomalli* K96243 strains were validated by fluorescence microscope. (FIGS. 11-12). The genomic DNA of both GFP- and RFP-tagged surrogates and hot strains were isolated. PCR analysis confirmed the correct reporter insertion at Tn7 site.

Bioinformatic Analyses (e.g. *Francisella tularensis*)

A gene expression dataset, (Wehrly, T. D. et al. (2009) *Intracellular biology and virulence determinants of Francisella tularensis revealed by transcriptional profiling inside macrophages*. Cell Microbiol 11(7):1128-50. NCBI GEO database) was used to identify three groups of *Francisella tularensis* gene transcripts that exhibited high, medium, and moderately low expression on average throughout the time series, as based on RMA-normalized Affymetrix probe set intensity levels. Each of these groups was then ranked for those transcripts that had the least variance as a function of time during macrophage infection. Of the transcripts that were identified in each tier, their relative position was used on the genome to identify those that were most likely in the 5' position of a potential operon, and the sequence upstream of that was used to test for potential promoter activity that could drive high, medium or low level GFP expression, respectively.

Monocyte-Derived Macrophages (MDMs) Infected with Chromosomally Integrated *Bacillus* sp., *Yersinia* sp., *Francisella tularensis* sp., and *Burkholderia* sp For MDM infection by *Bacillus* sp., *Yersinia* sp., *Francisella tularensis* sp., and *Burkholderia* sp, 7 day-old MDMs were grown in complete media (RPMI 1640, 10% heat inactivated FBS, 2 mM L-glutamine, 40 U/mL granulocyte-macrophage CSF, 100 U/mL macrophage CSF). The MDMs were treated with a suspension of *Bacillus* sp., *Yersinia* sp., *Francisella tularensis* sp., and *Burkholderia* sp (chromosomally integrated with the appropriate vector plasmids) in RPMI/10% human AB serum at a multiplicity of infection (MOI) of 50. MDMs were incubated with bacteria at 37° C., 5% $CO_2$ for 2 hrs and then washed 3 times with PBS and treated with appropriate antibiotics to kill extracellular *Bacillus* sp., *Yersinia* sp., *Francisella tularensis* sp., and *Burkholderia* sp. At various time points, cells were washed twice with PBS, treated with Live/Dead® Far Red viability stain in PBS for 30 minutes at 37° C., 5% $CO_2$, washed once with PBS, fixed with 4% PFA at room temperature, washed once with PBS and treated with 1 mM Hoechst 33342 in PBS. Cell images were captured at at various magnifications (e.g., 20× magnification) using various filter settings: e.g., nuclear (blue, 377/477 nm excitation/emission), phase contrast (no filter), GFP (green 485/524 nm excitation/emission), Live/Dead viability stain (red, 628/692 nm excitation/emission). Images were overlaid using Image J software.

All documents cited are incorporated herein by reference; the citation of any document is not to be construed as an admission that it is prior art with respect to the present invention.

Having described embodiments of the present invention in detail, and by reference to specific embodiments thereof, it will be apparent that modifications and variations are possible without departing from the scope of the embodiments defined in the appended claims. More specifically, although some aspects of embodiments of the present invention are identified herein as preferred or particularly advantageous, it is contemplated that the embodiments of the present invention are not necessarily limited to these preferred aspects.

What is claimed:

1. A method of screening candidate compounds for possessing anti-bacterial efficacy suitable for rapid response to contamination by a bacterial pathogen, the method comprising:

providing a modified bacterial pathogen, wherein the modification comprises integration with a vector plasmid, said vector plasmid engineered to constitutively express a chromosomal transcriptional fusion fluorescent protein that results in sustained fluorescence while the modified bacterial pathogen is alive, wherein the bacterial pathogen is selected from the group consisting of *Bacillus anthracis* Ames and *Bacillus anthracis* Stern, and the vector plasmid is selected from the group consisting of pBKJΔBla1-p0253-GFP, pBKJΔBla1-p0253-RFP, pBKJΔBla1-pntr-GFP, and pBKJΔBla1-pntr-RFP;

contacting a candidate compound with the modified bacterial pathogen;

determining whether the modified bacterial pathogen exhibits fluorescence; and identifying a candidate compound as comprising anti-bacterial efficacy where the fluorescence is extinguished.

2. The method of claim 1, wherein said method comprises a high throughput screening method.

3. The method of claim 2, wherein the step of identifying requires less than 200 ms.

4. The method according to claim 1, wherein the contamination results from intentional dissemination of the bacterial pathogen.

5. The method according to claim 4, wherein intentional dissemination results from bioterrorism.

6. The method of claim 1, wherein said chromosomal transcriptional fusion fluorescent protein is selected from the group consisting of optimized Green Fluorescent Protein (GFP) and optimized Red Fluorescent protein (RFP).

7. A method of responding to intentional bioterrorist dissemination of a known or unknown bacterial pathogen, the method comprising:

isolating a sample cell of the bacterial agent;

modifying the cell by inserting a vector plasmid engineered to constitutively express a chromosomal transcriptional fusion fluorescent protein that results in sustained fluorescence while the modified bacterial pathogen is alive, said vector plasmid selected from pBKJΔBla1-p0253-GFP, pBKJΔBla1-p0253-RFP, pBKJΔBla1-pntr-GFP, and pBKJΔBla1-pntr-RFP;

screening a library of anti-bacterial agents for efficacy against the known or unknown bacterial pathogen, said screening comprising the steps of: contacting a candidate compound with the modified bacterial pathogen;

determining whether the modified bacterial pathogen exhibits fluorescence; and identifying a candidate compound as comprising anti-bacterial efficacy against the known or unknown bacterial agent where the fluorescence is extinguished; treating the contamination with the identified antibacterial compound.

* * * * *